US008841491B2

(12) United States Patent
Fujii et al.

(10) Patent No.: US 8,841,491 B2
(45) Date of Patent: Sep. 23, 2014

(54) METHOD FOR PRODUCING FLUORENE DERIVATIVE

(75) Inventors: Katsuhiro Fujii, Hyogo (JP); Suguru Hata, Hyogo (JP); Kohta Fukui, Chiba (JP); Hiroyuki Kato, Osaka (JP); Yuki Numata, Hyogo (JP)

(73) Assignee: Taoka Chemical Co., Ltd., Osaka (JP)

( * ) Notice: Subject to any disclaimer, the term of this patent is extended or adjusted under 35 U.S.C. 154(b) by 421 days.

(21) Appl. No.: 13/263,029

(22) PCT Filed: Feb. 24, 2010

(86) PCT No.: PCT/JP2010/052854
§ 371 (c)(1),
(2), (4) Date: Oct. 5, 2011

(87) PCT Pub. No.: WO2010/119727
PCT Pub. Date: Oct. 21, 2010

(65) Prior Publication Data
US 2012/0029244 A1    Feb. 2, 2012

(30) Foreign Application Priority Data

Apr. 13, 2009 (JP) ................. 2009-097067
Jul. 27, 2009 (JP) ................. 2009-174808
Oct. 2, 2009 (JP) ................. 2009-230198

(51) Int. Cl.
C07C 41/40 (2006.01)
C07C 41/30 (2006.01)
B01J 27/188 (2006.01)
B01J 21/16 (2006.01)

(52) U.S. Cl.
CPC ............... C07C 41/40 (2013.01); C07C 41/30 (2013.01); C07C 2103/18 (2013.01); B01J 27/188 (2013.01); B01J 21/16 (2013.01)
USPC ........................................... 568/633

(58) Field of Classification Search
CPC .......... C07C 41/30; C07C 41/40; C07C 43/23
USPC ........................................... 568/633
See application file for complete search history.

(56) References Cited

U.S. PATENT DOCUMENTS

| | | | |
|---|---|---|---|
| 4,675,458 A | 6/1987 | Riemann et al. | |
| 5,629,456 A | 5/1997 | Yamada et al. | |
| 2007/0032607 A1 | 2/2007 | Fuji | |
| 2007/0100170 A1 | 5/2007 | Murase et al. | |
| 2010/0105961 A1 | 4/2010 | Fujii et al. | |

FOREIGN PATENT DOCUMENTS

| | | | |
|---|---|---|---|
| CN | 1856524 A | | 11/2006 |
| JP | 04-041450 A | | 2/1992 |
| JP | 06-145087 A | | 5/1994 |
| JP | 7-165657 A | | 6/1995 |
| JP | 09-124530 A | | 5/1997 |
| JP | 10-017517 A | | 1/1998 |
| JP | 10-045654 A | | 2/1998 |
| JP | 10-045655 A | | 2/1998 |
| JP | 10-045656 A | | 2/1998 |
| JP | 2000-191577 A | | 7/2000 |
| JP | 2002-047227 A | | 2/2002 |
| JP | 2003-221352 A | | 8/2003 |
| JP | 2005-104898 A | | 4/2005 |
| JP | 2007-023016 A | | 2/2007 |
| JP | 2007-197368 A | | 8/2007 |
| JP | 4140975 | | 6/2008 |
| JP | 2009-046416 A | | 3/2009 |
| JP | 2010-024248 | * | 2/2010 |
| JP | 2010-059098 A | | 3/2010 |
| JP | 2010-248095 A | | 11/2010 |

OTHER PUBLICATIONS

International Search Report for corresponding International Application No. PCT/JP2010/052854 mailed Mar. 23, 2010.
Form PCT/ISA/237 for International Application No. PCT/JP2010/052854 dated Mar. 23, 2010.
Taiwanese Office Action received in corresponding Taiwanese Application No. 99105680 dated Feb. 18, 2014 and English translation.

* cited by examiner

*Primary Examiner* — Rosalynd Keys
(74) *Attorney, Agent, or Firm* — Renner, Otto, Boisselle & Sklar, LLP

(57) ABSTRACT

A method for producing a fluorene derivative by reacting fluorenone with a phenol or a phenoxyalcohol in the presence of an acid catalyst includes: adding an alkali to an obtained reaction liquid containing a fluorene derivative; and concentrating a resultant mixture liquid without removing the alkali thus added and a reaction product of the alkali, thereby separating an unreacted phenol or unreacted phenoxyalcohol.

7 Claims, No Drawings

METHOD FOR PRODUCING FLUORENE DERIVATIVE

TECHNICAL FIELD

The present invention relates to a method for producing a fluorene derivative useful as a raw material of polyester, polyurethane, polycarbonate, epoxy resin, denatured acrylic resin, and the like.

BACKGROUND ART

A fluorene derivative is excellent in heat resistance and transparency, and therefore, recently, shows promise as a material for production of a polymer with high index of refraction (e.g., epoxy resin, polyester, polyether, and polycarbonate). The fluorene derivative shows promise as a raw material of an optical lens, film, plastic optical fiber, optical disc substrate, heat-resistant resin, and engineering plastic etc.

As a method for producing a fluorene derivative, there is disclosed a method for obtaining 9,9-bis(4-(2-hydroxyethoxy)phenyl)fluorene by reacting fluorenone with 2-phenoxyethanol by using sulfuric acid and a thiol serving as catalysts, which method includes (a) adding a lower aliphatic alcohol to a reaction liquid to dissolve a target substance and thereafter (b) adding water to precipitate and recover the target substance (refer to Patent Literature 1).

Further, there is disclosed a method of recovering phenoxyethanol by (a) recovering precipitated 9,9-bis(4-(2-hydroxyethoxy)phenyl)fluorene by filtration, (b) removing a lower aliphatic alcohol from a filtrate by distillation, and (c) adding water to a liquid remaining in a pot to separate a phenoxyethanol layer (refer to Patent Literature 2).

However, since this method uses a large amount of sulfuric acid, the sulfuric acid or sulfur component derived from the catalysts is mixed in obtained crystals. This causes problems such as coloration of finished products, reduction in purity, and reduction in stability. Further, in order to obtain high-purity finished products such as optical resin materials, it is necessary to repeat purification to remove sulfur. In addition, it is necessary to carry out complex operations so as to recover phenoxyethanol from the filtrate.

As methods for solving such problems, there are disclosed (a) a method of: adding, to a reaction solution obtained by reacting fluorenone with phenoxyethanol by using sulfuric acid and a thiol serving as catalysts, water and a solvent incompatible with water; and recovering 9,9-bis(4-(2-hydroxyethoxy)phenyl)fluorene from an organic phase (refer to Patent Literatures 3 and 4) and (b) a method of treating, with ion exchange resin, an organic phase containing 9,9-bis(4-(2-hydroxyethoxy)phenyl)fluorene (refer to Patent Literature 5). However, sulfur still remains in both methods. Therefore, the methods have not completely solved the problems such as deteriorations in hue and purity of finished products.

Further, there is disclosed a method of (a) reacting fluorenone with phenoxyethanol by using sulfuric acid and a thiol serving as catalysts, (b) adding an alkaline aqueous solution to an obtained acid reaction liquid, and thereafter (c) coprecipitating 9,9-bis(4-(2-hydroxyethoxy)phenyl)fluorene, i.e., target substance, and sulfate and (d) recovering a coprecipitated product by filtration (Patent Literature 6). However, according to this method, in order to separate the 9,9-bis(4-(2-hydroxyethoxy)phenyl)fluorene and sulfate contained in the coprecipitated product thus recovered by filtration, the target substance is partitioned into an organic phase by redissolving the coprecipitated product with an extract agent and thereafter the 9,9-bis(4-(2-hydroxyethoxy)phenyl)fluorene is recovered by crystallization and filtration. That is, it is necessary to carry out industrially complex filtration and recovery operations two or more times.

As a method using no sulfuric acid, there is disclosed a method that uses metal exchange type montmorillonite (refer to Patent Literature 7). However, according to this method, montmorillonite to be used is extremely expensive and is difficult to obtain in large amounts. Further, according to this method, it is necessary to produce a metal-substituted montmorillonite catalyst by reacting commercially available montmorillonite with a metal chloride. Moreover, since a thiol such as beta-mercaptopropionic acid serving as a promoter is used for the purpose of increasing reaction yield, sulfur is to be mixed in the finished products. Therefore, in order to obtain high-purity finished products, it is necessary to repeat purification so as to remove sulfur.

Further, the inventors of the present invention disclose, as a method using no sulfuric acid, a method of obtaining 9,9-bis(4-(2-hydroxyethoxy)phenyl)fluorene by reacting fluorenone with phenoxyethanol in the presence of a heteropoly acid serving as a catalyst, which method includes (a) partitioning a target substance into an organic phase by adding an extract agent constituted by water and an organic solvent to a reaction liquid and (b) recovering the target substance (refer to Patent Literature 8). Further, the inventors of the present invention propose: a method for producing 9,9-bis(4-(2-hydroxyethoxy)phenyl)fluorene from fluorenone and 2-phenoxyethanol in the presence of a heteropoly acid catalyst (Patent Literature 9); and a method for producing 9,9-bis(4-(2-hydroxyethoxy)phenyl)fluorene whose melting point is 160° C. to 166° C. (Patent Literature 10). Moreover, there is disclosed a method of obtaining a fluorene derivative by reacting fluorenone with a phenol by using hydrochloric acid and a thiol serving as catalysts, which method includes partitioning a target substance into an organic phase by using an extract agent and recovering the target substance (refer to Patent Literature 11). However, according to these methods, a reaction liquid contains a large amount of unreacted phenol or phenoxyalcohol, which is highly soluble in water. This may cause a reduction in liquid separability, and thus cause a deterioration in hue or purity. Further, these methods place a large burden on the environment, because a large amount of organic compounds such as phenols or phenoxyalcohols are mixed in an aqueous phase, and/or it is necessary to use a large amount of organic solvent for liquid separation. Therefore, these methods are not industrially advantageous.

Furthermore, there is disclosed a method of reacting fluorenone with phenoxyethanol in the presence of cation exchange resin, while carrying out dehydration so that water content of a liquid phase of the reaction system is 0.1 wt % or less (Patent Literature 12). Patent Literature 12 states that it is possible to isolate a high-purity fluorenone derivative even by a general-purpose method. However, with this method, it is necessary to control water content of the reaction liquid. The control of the water content becomes more difficult and complex as the scale of the reaction increases. Further, this may reduce yield or purity. In addition, according to the study carried out by the inventors of the present invention, it is necessary to use strongly acidic ion exchange resin having a sulfonic acid group in order to cause reaction to proceed effectively. Due to impurities to be eluted from the ion exchange resin, a mere combination of general-purpose purifying operations may not be capable of achieving hue and purity that are required for materials for optical use.

Further, as described earlier, in recent years, a fluorene derivative such as 9,9-bis(4-(2-hydroxyethoxy)phenyl)fluorene has been used as a raw material of for example optical polycarbonate resin. For such use, it is required more than ever to produce, at high yield and at low cost, non-colored and high-purity finished products that contain no reaction by-products and no sulfur component.

Generally, in order to obtain a high-purity finished product by reacting fluorenone with a phenoxyalcohol or a phenol, it is required to reduce by-products in a reaction process. Other ways to reduce by-products to some extend include a process of neutralizing an obtained reaction mixture and a process of purifying an obtained product. Further, various conditions in the process of neutralizing the obtained reaction mixture and the process of purifying the obtained product are important for obtaining an non-colored finished product.

Usually, by-products are less generated as a reaction temperature decreases. Note, however, that a rate of reaction is inevitably reduced. Further, although the process of neutralizing the obtained reaction mixture and the process of purifying the obtained product would achieve improvement in purity of finished products and reduction in by-products and suppression of coloration, the yield of the finished products may decrease. Therefore, in order to obtain non-colored high-purity finished products at high yield, it is important to optimally combine the processes having optimum operation conditions throughout the entire production process. Under such circumstances, it is strongly desired to find such an optimum production method.

CITATION LIST

Patent Literatures

Patent Literature 1
Japanese Patent Application Publication, Tokukaihei, No. 7-165657 A (Publication Date: Jun. 27, 1995)
Patent Literature 2
Japanese Patent Application Publication, Tokukaihei, No. 10-17517 A (Publication Date: Jan. 20, 1998)
Patent Literature 3
Japanese Patent Application Publication, Tokukaihei, No. 10-45655 A (Publication Date: Feb. 17, 1998)
Patent Literature 4
Japanese Patent Application Publication, Tokukaihei, No. 10-45656 A (Publication Date: Feb. 17, 1998)
Patent Literature 5
Japanese Patent Application Publication, Tokukaihei, No. 10-45654 A (Publication Date: Feb. 17, 1998)
Patent Literature 6
Japanese Patent Application Publication, Tokukai, No. 2005-104898 A (Publication Date: Apr. 21, 2005)
Patent Literature 7
Japanese Patent Application Publication, Tokukai, No. 2000-191577 A (Publication Date: Jul. 11, 2000)
Patent Literature 8
Japanese Patent Application Publication, Tokukai, No. 2007-197368 A (Publication Date: Aug. 9, 2007)
Patent Literature 9
Japanese Patent Application Publication, Tokukai, No. 2007-23016 A (Publication Date: Feb. 1, 2007)
Patent Literature 10
Japanese Patent No. 4140975 B (Publication Date: Jun. 20, 2008)
Patent Literature 11
Japanese Patent Application Publication, Tokukai, No. 2002-47227 A (Publication Date: Feb. 12, 2002)
Patent Literature 12
Japanese Patent Application Publication, Tokukai, No. 2009-46416 A (Publication Date: Mar. 5, 2009)

SUMMARY OF INVENTION

Technical Problem

An object of the present invention is to provide a method for producing a high-purity fluorene derivative with good hue, which method places a smaller burden on the environment and is suitable for industrial use.

A further object of the present invention is to provide a method for producing a high-purity fluorene derivative that has good hue and is suitably usable as a resin material at high yield in an industrially stable manner, and also in an economically advantageous manner.

Solution to Problem

The inventors of the present invention diligently worked to attain the above object. As a result, the inventors of the present invention have made the following findings, and completed the present invention. That is, after adding an alkali to a reaction mixture liquid, which contains a fluorene derivative and is obtained by reacting fluorenone with a phenol or a phenoxyalcohol of formula (I) in the presence of an acid catalyst, an unreacted phenol or unreacted phenoxyalcohol can be separated and recovered without degrading the target substance by directly concentrating the reaction mixture liquid without removing an alkali thus added and a reaction product of the alkali. This makes it possible to obtain a fluorene derivative that has good hue and is excellent as a polymer material. Further, this production method imposes a smaller burden on the environment because less organic solvent is required and a burden of waste water treatment is smaller etc., and therefore is industrially advantageous.

That is, the present invention provides the following [1] through [8].

[1] A method for producing a fluorene derivative of formula (II)

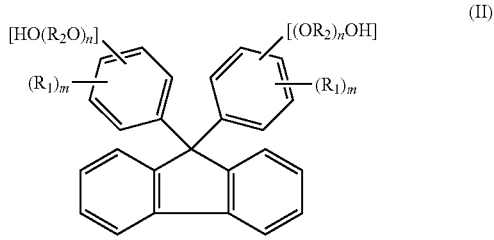

(wherein $R_2$ is an alkylene group; $R_1$ is selected from an alkyl group, a cycloalkyl group, an aryl group, an aralkyl group, an alkoxy group, and a halogen atom; n is 0 or an integer of 1 or greater; and m is 0 or an integer of 1 to 4, with the proviso that when m is 0, n is an integer of 1 or greater)

by reacting fluorenone with a compound of formula (I)

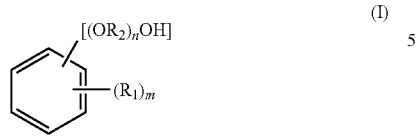

(wherein $R_2$ is an alkylene group; $R_1$ is selected from an alkyl group, a cycloalkyl group, an aryl group, an aralkyl group, an alkoxy group, and a halogen atom; n is 0 or an integer 1 or greater; and m is 0 or an integer of 1 to 4, with the proviso that when m is 0, n is an integer of 1 or greater) in the presence of an acid catalyst, said method, including the steps of: reacting the fluorenone with the compound of formula (I) in the presence of the acid catalyst to obtain a reaction mixture liquid that contains the fluorene derivative of formula (II); and after addition of an alkali to the reaction mixture liquid that contains the fluorene derivative after completion of reaction, concentrating the reaction mixture liquid without removing the alkali thus added and a reaction product of the alkali, thereby separating an unreacted compound of formula (I).

[2] The method according to [1], wherein, in the step of reacting, the fluorenone and the compound of formula (I) are reacted under reduced pressure.

[3] The method according to [1] or [2], wherein the compound of formula (I) is methyl phenol or phenoxyethanol.

[4] The method according to [3], wherein: the compound of formula (I) is phenoxyethanol; and the fluorenone and the compound of formula (I) are reacted under a reduced pressure of not more than $39\times10^3$ Pa at a temperature between 30° C. and 150° C.

[5] The method according to [3], wherein: the compound of formula (I) is methyl phenol; and the fluorenone and the compound of formula (I) are reacted under a reduced pressure of not more than $30\times10^3$ Pa at a temperature between 30° C. and 95° C.

[6] The method according to any one of [1] through [5], wherein the unreacted compound of formula (I) separated in the step of concentrating is recycled to the step of reacting so as to be used as a raw material.

[7] A method according to any one of [1] through [6], further including the steps of: extracting the fluorene derivative by adding an extract agent constituted by water and an organic solvent separable from water to a concentrated liquid obtained in the step of concentrating to partition the fluorene derivative into an organic phase, and thereafter separating an aqueous phase; and precipitating a crystal of the fluorene derivative by cooling the organic phase, and thereafter filtering the organic phase to recover the crystal.

[8] A method for producing 9,9-bis(4-(2-hydroxyethoxy)phenyl)fluorene by reacting fluorenone with phenoxyethanol in the presence of an acid catalyst, said method, including the step of: reacting the fluorenone with the phenoxyethanol under a reduced pressure of not more than $39\times10^3$ Pa at a temperature between 30° C. and 150° C.

Advantageous Effects of Invention

According to the present invention, it is possible to provide a method for producing a fluorene derivative by reacting fluorenone with a phenol or a phenoxyalcohol in the presence of an acid catalyst, which method produces a finished product excellent as a polymer material in an industrially advantageous manner in which the burden on the environment is reduced.

DESCRIPTION OF EMBODIMENTS

The following description discusses an embodiment of the present in detail. Note, however, that the present invention is not limited to the following description.

(i)
A method for producing a fluorene derivative in accordance with the present invention includes (a) adding an alkali to a reaction liquid obtained by reacting fluorenone with a phenol or a phenoxyalcohol of formula (I) in the presence of an acid catalyst and (b) separating an unreacted phenol or unreacted phenoxyalcohol from the reaction liquid without removing an added alkali and its reaction product.

Specifically, a method for producing a fluorene derivative in accordance with the present invention is a method for producing a fluorene derivative of formula (II)

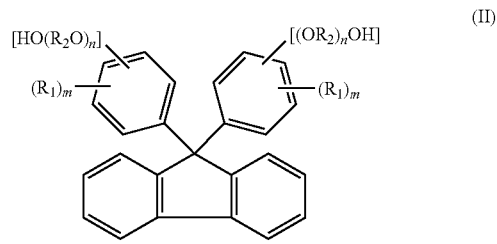

by reacting fluorenone with a compound of formula (I)

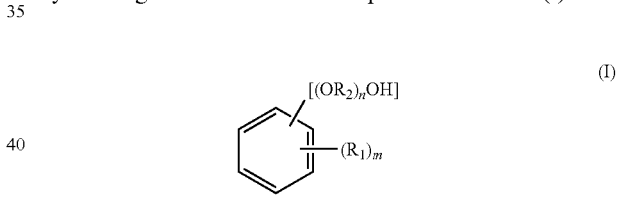

in the presence of an acid catalyst, said method, including the steps of: reacting the fluorenone with the compound of formula (I) in the presence of the acid catalyst to obtain a reaction mixture liquid that contains the fluorene derivative of formula (II); and after addition of an alkali to the reaction mixture liquid that contains the fluorene derivative after completion of reaction, concentrating the reaction mixture liquid without removing the alkali thus added and a reaction product of the alkali, thereby separating an unreacted compound of formula (I).

The compound of formula (I) corresponds to a phenol group or a phenoxyalcohol group substituted at 9-position in the fluorene derivative of formula (II).

A substituent represented by $R_1$ is not particularly limited. Examples of the substituent include: $C_1$-$C_{20}$ alkyl groups such as methyl, ethyl, propyl, butyl, and t-butyl groups; $C_5$-$C_{16}$ cycloalkyl groups such as cyclopentyl and cyclohexyl groups; $C_6$-$C_{16}$ aryl groups such as phenyl and alkyl phenyl groups; $C_7$-$C_{16}$ aralkyl groups such as benzyl and phenethyl groups; $C_1$-$C_{12}$ alkoxy groups such as methoxy and ethoxy groups; and halogen atoms such as fluorine and chlorine atoms. More preferred substituents are $C_1$-$C_6$ alkyl groups, $C_1$-$C_6$ alkoxy groups, $C_6$-$C_{10}$ cycloalkyl groups, and $C_6$-$C_{10}$ aryl groups. Particularly preferred substituents are $C_1$-$C_4$ alkyl groups. $R_1$ may be the same or different in a single benzene ring. A position at which $R_1$ substitutes is not particularly limited. The number m of the substituent(s) is 0 or 1 to 4, preferably 0 to 2, and further preferably 0 or 1.

An alkylene group represented by $R_2$ is not particularly limited. Examples of the alkylene group include ethylene, propylene, trimethylene, tetramethylene, and hexamethylene groups. The alkylene group is preferably a $C_2$-$C_6$ alkylene group, and further preferably a $C_2$-$C_3$ alkylene group. The number n of the substituent(s) is 0 or 1 or greater, preferably 0 to 15, and further preferably 0 to 5. Note here that, in a case where n is 2 or greater, the polyalkoxy group may be constituted by the same alkoxy groups or may be constituted by different alkoxy groups (e.g., ethoxy group and propyleneoxy group). However, usually, the polyalkoxy group is constituted by the same alkoxy groups. In a case where m is 0, n is 1 or greater.

As the compound of formula (I), a compound in which $R_1$ is a $C_1$-$C_4$ alkyl group, $R_2$ is a $C_2$-$C_6$ alkylene group, and n is an integer of 0 to 5 is suitably usable.

Specific examples of the compound of formula (I) include compounds in which n=0, compounds in which n=1, and compounds in which n=2 or greater. Examples of the compounds in which n=0 include: alkylphenols such as 2-methyl phenol and 3-methyl phenol; dialkyl phenols such as 2,3-xylenol, 2,6-xylenol, and 3,5-xylenol; alkoxyphenols such as 2-methoxy phenol and 2-ethoxy phenol; and phenylphenols such as 2-phenylphenol and 3-phenylphenol. Examples of the compounds in which n=1 include phenoxyalkyl alcohols such as phenoxyethanol, phenoxypropanol, and phenoxybutanol; alkyl phenoxyalkyl alcohols such as (2-methyl-phenoxy) ethanol, (3-methyl-phenoxy)ethanol, (3-ethyl-phenoxy) ethanol, (3-butyl-phenoxy)ethanol, (2-methyl-phenoxy)propanol, and (3-methyl-phenoxy)propanol; dialkyl phenoxyalkyl alcohols such as (2,3-dimethylphenoxy)ethanol, (2,5-dimethylphenoxy)ethanol, (2,6-dimethylphenoxy) ethanol, and (2,6-dibutylphenoxy)ethanol; alkoxy phenoxyalkyl alcohols such as (2-methoxy phenoxy)ethanol; cycloalkyl phenoxyalkyl alcohols such as (2-cyclohexylphenoxy)ethanol; and aryl phenoxyalkyl alcohols such as biphenylyl oxyethanol. Examples of the compounds in which n=2 or greater include: polyoxy alkylene phenyl ethers corresponding to the above phenoxyalkyl alcohols. Among these, particularly useful as the compound of formula (I) is methyl phenol or phenoxyethanol.

The amount of the compound of formula (I) to be used is not particularly limited. In view of side reaction inhibition and economical efficiency, usually, the amount is preferably 2 mol to 50 mol, more preferably 3 mol to 50 mol, further preferably 4 mol to 20 mol, and particularly preferably 4 mol to 10 mol, relative to 1 mol of fluorenone. The compound can be also used as a reaction solvent.

The acid catalyst for use in the present invention is not particularly limited. Examples of the acid catalyst include: hydrochloric acid, sulfuric acid, phosphoric acid, organic acids, ion exchange resin, heteropoly acids, and other inorganic solid catalysts (metal oxide, metal sulfide, phosphoric acid, clay mineral, zeolite, kaolin, and the like). These catalysts are used individually or a mixture of two or more catalysts is used. Among these, hydrochloric acid, sulfuric acid, ion exchange resin, or heteropoly acids is particularly preferred. In a case of using a catalyst other than heteropoly acids, it is preferable to use, together with the catalyst, a thiol serving as a promoter.

A hydrochloric acid for use in the present invention is for example a 5 wt % to 36 wt % hydrogen chloride aqueous solution, preferably a 20 wt % to 36 wt % hydrogen chloride aqueous solution. Sulfuric acid for use in the present invention is for example dilute sulfuric acid, 90% or more concentrated sulfuric acid, fuming sulfuric acid, or the like.

Ion exchange resin for use in the present invention is for example strongly acidic cation exchange resin having a sulfonic acid group or weakly acidic cation exchange resin having a carboxylic acid group. The structure of the ion exchange resin may be (a) of a gel type having micropores or (b) of a porous type having not only micropores but also macropores in particles. Among the above ion exchange resin, strongly acidic cation exchange resin is preferred, and porous type strongly acidic cation exchange resin is particularly preferred.

As the ion exchange resin, commercially available ion exchange resin such as for example DIAION (registered trademark, manufactured by Mitsubishi Chemical Corporation), AMBERLYST (registered trademark, manufactured by ORGANO CORPORATION), Lewatit (registered trademark, manufactured by LANXESS), DOWEX (registered trademark, manufactured by The Dow Chemical Company), DUOLITE (registered trademark, manufactured by Sumitomo chemical Co., Ltd.), or Nafion (registered trademark, manufactured by DuPont) can be used.

A heteropoly acid for use in the present invention is generally (a) a complex oxide acid constituted by a complex of two or more different oxides or (b) the complex oxide acid in which part or all of protons thereof have been replaced by other cation(s). The heteropoly acid is constituted by for example: an oxyacid ion (e.g., phosphoric acid, silicic acid) of an element such as phosphorus, arsenic, tin, silicon, titanium, or zirconium; and an oxyacid ion (e.g., vanadic acid, molybdic acid, tungstic acid) of an element such as molybdenum, tungsten, vanadium, niobium, or tantalum. Various heteropoly acids can be obtained by changing the combination of such oxyacid ions. Specific examples of the heteropoly acid include molybdophosphoric acid, tungstophosphoric acid, molybdosilicic acid, tungstosilicic acid, and molybdo vanado phosphoric acid. The heteropoly acid may be anhydrous or may contain water of crystallization. Further, the heteropoly acid may be supported on a carrier such as activated carbon, alumina, silica-alumina, and diatom earth. These heteropoly acids may be used independently or two or more heteropoly acids can be used in combination.

Examples of a thiol used as a promoter as needed in the present invention include: mercaptocarboxylic acids such as thioacetic acid, beta-mercapto propionic acid, alpha-mercapto propionic acid, thioglycolic acid, thiooxalic acid, mercapto succinic acid, and mercapto benzoic acid; alkyl mercaptans such as methyl mercaptan, ethyl mercaptan, propyl mercaptan, isopropyl mercaptan, n-butyl mercaptan, and dodecyl mercaptan; and aralkyl mercaptans such as benzyl mercaptan. These thiols can be used independently, or two or more thiols can be used in combination.

The fluorenone for use in the present invention is not particularly limited. Note, however, that it is preferable to use high-purity fluorenone that is hardly colored and further has high transmittance when dissolved in a solvent, because reaction and purification of such fluorenone are easy and therefore it is possible to efficiently produce a fluorene derivative.

Specific examples of the fluorene derivative of formula (II) include: 9,9-bis(hydroxy(poly)alkoxyphenyl)fluorene, 9,9-bis(hydroxy(poly)alkoxy-alkylphenyl)fluorene, 9,9-bis(hydroxy(poly)alkoxy-dialkylphenyl)fluorene, 9,9-bis(hydroxy(poly)alkoxy-alkoxyphenyl)fluorene, 9,9-bis(hydroxy(poly)alkoxy-cycloalkylphenyl)fluorene, and 9,9-bis(hydroxy(poly)alkoxy-arylphenyl)fluorene. Among these, the present invention is further advantageous in producing 9,9-bis(hydroxy(poly)alkoxyphenyl)fluorene or 9,9-bis(hydroxy(poly) alkoxy-alkylphenyl)fluorene. The present invention is particularly advantageous in producing 9,9-bis(4-(2-hydroxyethoxy)phenyl)fluorene, 9,9-bis(4-hydroxy-3-methylphenyl)fluorene, or 9,9-bis(4-hydroxy-2-methylphenyl)fluorene.

In the present invention, how to carry out the reaction of fluorenone and the compound of formula (I) is not particularly limited. Usually, the reaction can be carried out by (a) feeding fluorenone, a phenol or a phenoxyalcohol, and an acid catalyst into a reaction apparatus, and (b) heating and stirring a mixture in air or under inert gas atmosphere such as nitrogen or helium, in the presence or absence of an inert solvent such as toluene or xylene. The reaction temperature and the amount of the acid catalyst can be various changed depending on the type of the acid catalyst to be used.

After the reaction, an alkali is added to an obtained reaction liquid. Thereafter, from the reaction liquid, all or part of an unreacted phenol or unreacted phenoxyalcohol is distilled away without removing the alkali thus added and a reaction product of the alkali, thereby the reaction solution is concentrated.

Examples of the alkali for use in the present invention include: alkali metal hydroxides such as sodium hydroxide and potassium hydroxide; alkali metal carbonates such as sodium carbonate, sodium hydrogencarbonate and potassium hydrogencarbonate; alkali earth metal hydroxides such as calcium hydroxide and magnesium hydroxide; alkali earth metal carbonates such as calcium carbonate; and ammonia. Among these, alkali metal hydroxides are preferred, and sodium hydroxide is particularly preferred. The alkali may be added directly as a solid, but usually is added as an aqueous solution. The amount of the alkali to be used is not particularly limited, provided that the amount is greater than or equal to the amount that deactivates the effect of the catalyst. Usually, the amount is 0.9 to 2.0 equivalents, preferably 1.0 to 1.5 equivalents, relative to 1 equivalent of the catalyst. If the amount of the alkali is large, the alkali may remain in the finished product and may cause coloration. If the amount of the alkali is small, by-products may be generated during concentration and purity and yield may be reduced.

In a case where the unreacted phenol or unreacted phenoxyalcohol is distilled away from the reaction liquid and the reaction liquid is concentrated without adding an alkali, a remaining catalyst accelerates generation of by-products, and thus causes deteriorations in purity and hue, and a reduction in yield. Note however that, since an alkali is added as above, it is possible, by concentrating the reaction liquid, to distill away and recover an excess phenol or excess phenoxyalcohol without causing reductions in purity and yield etc. of the finished products. The phenol or phenoxyalcohol thus recovered can be directly reused as a raw material.

A concentration condition in which an unreacted phenol or unreacted phenoxyalcohol is distilled away and the reaction solution is concentrated is not particularly limited. Usually, the concentration is carried out under reduced pressure at a temperature of not more than 170° C., preferably 30° C. to 160° C., and further preferably 50° C. to 160° C. High concentration temperatures may degrade the fluorene derivative and cause a reduction in yield. Further, as to the unreacted phenol or unreacted phenoxyalcohol, it is preferable to distill away as many as possible of them. Note however that, in a case where removal of the unreacted phenol or unreacted phenoxyalcohol causes precipitation of crystals in a concentrated liquid, a subsequent operation can be carried out with respect to the concentrated liquid in which part of the unreacted phenol or unreacted phenoxyalcohol remains.

After the concentration, an extract agent constituted by water and an organic solvent separable from water is added to the concentrated liquid to partition the fluorene derivative into an organic phase. Then, the fluorene derivative is recovered. The organic phase thus obtained can be directly subjected to precipitation of fluorene derivative crystals. Note however that, usually, the organic phase is washed with water and dehydrated etc., and then subjected to precipitation of fluorene derivative crystals by cooling crystallization. The crystals thus precipitated are recovered by for example filtration. The crystals thus obtained may be washed with a solvent used in the crystallization and/or may be dried.

That is, the method for producing the fluorene derivative in accordance with the present invention preferably further includes the steps of: extracting the fluorene derivative by adding an extract agent constituted by water and an organic solvent separable from water to a concentrated liquid obtained in the step of concentrating to partition the fluorene derivative into an organic phase, and thereafter separating an aqueous phase; and precipitating a crystal of the fluorene derivative by cooling the organic phase, and thereafter filtering the organic phase to recover the crystal.

Examples of the organic solvent separable from water for use in the purification include: aromatic hydrocarbon solvents such as benzene, toluene, xylene, and mesitylene; halogenated aromatic hydrocarbons such as chlorobenzene and dichlorobenzene; aliphatic hydrocarbons such as pentane, hexane, and heptane; halogenated aliphatic hydrocarbon solvents such as dichloromethane and 1,2-dichloroethane; aliphatic ethers such as diethyl ether, di-iso-propyl ether, methyl-tert-butyl ether, and diphenyl ether; and ester solvents such as ethyl acetate and butyl acetate. Among these, aromatic hydrocarbon solvents or aliphatic hydrocarbons solvents are more preferred, aromatic hydrocarbon solvents are further preferred, and toluene or xylene is particularly preferred. The amount of the organic solvent is not particularly limited. Usually, in view of economic efficiency, the amount is preferably not less than 0.5 times by weight, preferably 1 to 100 times by weight, and further preferably 1 to 20 times by weight, relative to fluorenone.

(ii)

Further, the inventors of the present invention have diligently worked to attain the object of providing a method for producing a high-purity fluorene derivative with good hue at high yield in the industrially stable manner and also in the economically advantageous manner. As a result, the inventors of the present invention have found that it is possible to stably and easily produce a fluorene derivative such as 9,9-bis(4-(2-hydroxyethoxy)phenyl)fluorene (a) in which not only contents of remaining phenoxyethanol or by-products but also sodium content and/or sulfur content which are minor constituents are extremely small and (b) which is excellent as a resin material, particularly as a resin material for optical products, by (A) optimizing the reacting step, concentrating step, extracting step, precipitating and filtering step, and step of recycling phenoxyethanol, and (B) optimally combining such steps. Then, the inventors of the present invention have completed the present invention.

(ii-1) Reacting Step

In the reacting step, fluorenone and the compound of formula (I) may be reacted at normal pressures. Note, however, that fluorenone and the compound of formula (I) are reacted more preferably under reduced pressure.

This reduces reaction time and suppresses generation of by-products, thereby allowing easy purification. Accordingly, it is possible to produce a fluorene derivative excellent as a polymer material in a more economically advantageous manner.

Also in a case where fluorenone and the compound of formula (I) are reacted under reduced pressure, usually, the reaction can be carried out by (a) feeding the fluorenone, the compound of formula (I), and an acid catalyst into a reaction apparatus and (b) heating and stirring a mixture under reduced pressure in air or in an inert gas such as nitrogen or helium.

Pressure applied when the fluorenone and the compound of formula (I) are reacted under reduced pressure may be determined as appropriate depending on the compound of formula (I) to be used.

<Case where Phenoxyalcohol is Used>

For example, in a case where the compound of formula (I) is a phenoxyalcohol such as phenoxyethanol, it is preferable to react fluorenone with the phenoxyalcohol under a reduce pressure of not more than $39 \times 10^3$ Pa at a temperature between 30° C. and 150° C.

As a more specific embodiment of the method for producing the fluorene derivative in accordance with the present invention, the following description discusses a further preferable reaction condition for the case where phenoxyethanol is used as the compound of formula (I).

That is, according to the method of the present embodiment, in the reacting step, fluorenone and phenoxyethanol are reacted under reduced pressure in the presence of an acid catalyst to obtain a reaction mixture liquid containing 9,9-bis (4-(2-hydroxyethoxy)phenyl)fluorene.

The reaction mixture liquid thus obtained contains not only the 9,9-bis(4-(2-hydroxyethoxy)phenyl)fluorene (i.e., target subject), unreacted phenoxyethanol and the catalyst, but also by-products such as an isomer of 9,9-bis(4-(2-hydroxyethoxy)phenyl)fluorene, and a dimer, trimer, bisphenol, and trisphenol etc. of 9,9-bis(4-(2-hydroxyethoxy)phenyl)fluorene.

The amount of phenoxyethanol to be used in the present embodiment is not particularly limited. The excess amount of phenoxyethanol relative to fluorenone makes it possible to increase yield and reaction efficiency. Specifically, the amount of phenoxyethanol is preferably 2 mol to 50 mol, more preferably 3 mol to 20 mol, and further preferably 5 mol to 15 mol, relative to 1 mol of fluorenone. Too small an amount of phenoxyethanol tends to cause an increase in by-products, thereby causing reductions in purity and yield. Too large an amount of phenoxyethanol reduces economical efficiency.

According to the present embodiment, the fluorenone and phenoxyethanol are reacted usually in the absence of a solvent. Note, however, that the fluorenone and phenoxyethanol can be reacted under reduced pressure in the presence of a solvent as needed, provided that the object of the present invention is attained. Examples of a solvent include: aromatic hydrocarbon solvents such as toluene and xylene; halogenated aromatic hydrocarbon solvents such as chlorobenzene and dichlorobenzene; aliphatic hydrocarbon solvents such as pentane, hexane and heptane; and halogenated aliphatic hydrocarbon solvents such as dichloromethane and 1,2-dichloroethane.

The acid catalyst for use in the present embodiment is not particularly limited, and the acid catalysts described in the above (i) can be suitably used. Among those, heteropoly acids and ion exchange resin are more preferred, because (a) these catalysts can be separated from the reaction mixture liquid after completion of the reaction by a simple operation such as filtration and (b) a continuous reaction is available by using a flowing reaction apparatus filled with such catalysts. Further, heteropoly acids are particularly preferred among the above, because fewer components are eluted therefrom and a higher-purity target substance with better hue can be obtained.

The heteropoly acids described in the above (i) can be suitably employed as the heteropoly acid that is particularly preferred in the present embodiment.

The amount of the heteropoly acid to be used is not particularly limited. In order to achieve a sufficient rate of reaction, the amount is not less than 0.0001 times by weight, preferably 0.001 to 30 times by weight, and further preferably 0.01 to 5 times by weight, relative to fluorenone.

The reaction temperature in the present embodiment varies depending on the amount of phenoxyethanol to be used, the type of acid catalyst, and degree of pressure reduction. The reaction temperature is preferably 30° C. to 150° C., more preferably 90° C. to 150° C., and further preferably 100° C. to 140° C. Reaction temperatures of not more than 150° C. suppress an increase in generation of by-products and thus improve purity and yield. Further, the reaction temperatures of not more than 150° C. prevent coloration of the finished product. Therefore, the reaction temperatures of not more than 150° C. are preferred. Temperatures of not less than 30° C. are preferred because, at such temperatures, the reaction proceeds in a favorable manner and time taken for completion of the reaction is not long.

The reduced pressure in the present embodiment is preferably not more than $39 \times 10^3$ Pa, more preferably not more than $14 \times 10^3$ Pa, and further preferably between $6.7 \times 10^3$ Pa and $0.3 \times 10^3$ Pa. The reduced pressure of not more than $39 \times 10^3$ Pa is preferred, because the reaction proceeds in a favorable manner or time taken for completion of the reaction is not too long even at reaction temperatures of not more than 150° C. In a case of a reflux dehydration reaction using an azeotropic dehydration solvent, the reaction may proceed at normal pressures at temperatures of not more than 150° C. Note, however, that the reduced pressure of not more than $39 \times 10^3$ Pa is preferred because, under such a reduced pressure, time taken for completion of the reaction is not too long. Meanwhile, as the reaction scale increases, the reaction time tends to increase. Also in this regard, the above reduced pressure is preferred because the time taken for completion of the reaction is not too long and therefore the amount of by-products is not too large. According to the method of the present embodiment, volume efficiency during the reaction is increased, and the reaction time is reduced. Further, the method of the present embodiment is largely unaffected by equipment and the reaction scale, and is capable of suppressing generation of by-products. This achieves easy purification, and makes it possible to obtain finished products with stable quality.

Accordingly, it is possible to provide a method for producing 9,9-bis(4-(2-hydroxyethoxy)phenyl)fluorene by condensation reaction of fluorenone and phenoxyethanol, which method is suitable for industrial use and is capable of producing high-purity 9,9-bis(4-(2-hydroxyethoxy)phenyl)fluorene with good hue in an economically advantageous manner.

Other reaction conditions are not particularly limited. In a case where phenoxyethanol is distilled out of the reaction system during reaction, the phenoxyethanol thus distilled out may be directly removed out of the reaction system. Alternatively, the reaction can be carried out while the phenoxyethanol is being separated from distilled water and then fed back to the reaction system. The reaction may be carried out batch-wise or continuously.

<Case where Phenol is Used>

In a case where the compound of formula (I) is for example a phenol such as methyl phenol, it is preferable to react fluorenone with the phenol under a reduced pressure of not more than $30 \times 10^3$ Pa at a temperature of 30° C. to 95° C.

As more specific another embodiment of the method for producing the fluorene derivative in accordance with the present invention, the following description discusses a more preferable reaction condition for the case where methyl phenol is used as the compound of formula (I).

That is, according to the method of the present embodiment, in the reacting step, fluorenone and methyl phenol are reacted under reduced pressure in the presence of an acid catalyst to obtain a reaction mixture liquid containing 9,9-biscresol fluorene.

The methyl phenol for use in the present embodiment is for example o-cresol, m-cresol, or p-cresol. These cresols may be used independently or a mixture of two or more cresols may be used. Among these, o-cresol is more preferred. The amount of the cresol to be used is not particularly limited. In view of workability and economical efficiency, usually, the amount is 11 mol to 25 mol, preferably 11 mol to 20 mol, relative to 1 mol of fluorenone. The cresol of less than 11 times by mol may lead to a condition where crystals (product) are precipitated during reaction, and lead to causing a deterioration in workability. The cresol of more than 25 times by mol will cause a reduction in economic efficiency.

The acid catalyst for use in the present embodiment is not particularly limited, and is the same as in the case where phenoxyethanol is used as the compound of formula (I). Therefore, the description for the acid catalyst is omitted here.

The reaction temperature in the present embodiment varies depending on the type of solvent and degree of pressure reduction. The reaction temperature is 30° C. to 95° C., preferably 40° C. to 80° C., and further preferably 55° C. to 80° C. Reaction temperatures of not more than 95° C. suppress an increase in by-products and thus improve purity and yield. Further, the reaction temperatures of not more than 95° C. prevent coloration of the finished product. Therefore, the reaction temperatures of not more than 95° C. are preferred. Temperatures of not less than 30° C. are preferred because, at such temperatures, the reaction proceeds in a favorable manner and time taken for completion of the reaction is not long.

The reduced pressure in the present embodiment is not more than $30 \times 10^3$ Pa, preferably not more than $7 \times 10^3$ Pa, and further preferably $0.5 \times 10^3$ Pa to $3 \times 10^3$ Pa. If a reduced pressure is not more than $30 \times 10^3$ Pa and a reaction temperature is 30° C. to 95° C., then resultant 9,9-biscresol fluorene is less colored and is suitably usable industrially.

The reaction of fluorenone with a phenol can be carried out by for example (a) feeding the fluorenone, phenol and heteropoly acid into a reaction apparatus and (b) heating and stirring a mixture. In such a case, by carrying out the reaction under a dehydrated condition where water (such as water containing a catalyst or reaction product water) inside the reaction system is being removed, the reaction is accelerated as compared to a case where water inside the reaction system is not removed. This suppresses generation of by-products.

In the present embodiment, the reaction under reduced pressure can be carried out with use of an azeotropic dehydration solvent as needed, provided that the object of the present invention is attained. The azeotropic dehydration solvent for use in the reaction is not particularly limited. Examples of the azeotropic dehydration solvent include: aromatic hydrocarbon solvents such as toluene and xylene; halogenated aromatic hydrocarbon solvents such as chlorobenzene and dichlorobenzene; aliphatic hydrocarbon solvents such as pentane, hexane, and heptane; halogenated aliphatic hydrocarbon solvents such as dichloromethane and 1,2-dichloroethane, aliphatic ether solvents and cyclic ether solvents such as diethyl ether, di-iso-propyl ether, methyl-t-butyl ether, diphenyl ether, tetrahydrofuran, and dioxane; ester solvents such as ethyl acetate and butyl acetate; nitrile solvents such as acetonitrile, propionitrile, butyronitrile, and benzonitrile; and amide solvents such as N,N-dimethylformamide, N,N-dimethylacetamide, and 1-methyl-2-pyrrolidinone. Among these, aromatic hydrocarbon solvents and halogenated aromatic hydrocarbon solvents are more preferred as the azeotropic dehydration solvent, and toluene, xylene, chlorobenzene, and dichlorobenzene are further preferred as the azeotropic dehydration solvent. The amount of the azeotropic dehydration solvent to be used is not particularly limited. Usually, the amount is not more than 10 parts by weight, preferably not more than 5 parts by weight, and further preferably not more than 2 parts by weight, relative to fluorenone. While an appropriate amount of the solvent accelerates the reaction, an excess amount of the solvent may reduce a rate of the reaction.

(ii-2) Concentrating Step

In the concentrating step, there is no particular limitation as to the amount of the phenol such as methyl phenol or the phenoxyalcohol such as phenoxyethanol which remains in an obtained concentrated liquid. Usually, the amount of the phenol or phenoxyalcohol remaining in the concentrated liquid is not more than 10 wt %, preferably not more than 5 wt %, relative to the concentrated liquid. The amount of the phenol or phenoxyalcohol remaining in the concentrated liquid is preferably not more than 5 wt %, because this amount achieves good liquid separability in the extracting step. The amount of not more than 5 wt % is preferred also for the following reason. Since the phenol or phenoxyalcohol is hardly likely to be mixed into generated waste water, the waste water is less likely to show a high TOC (total organic carbon), high COD (chemical oxygen demand), high BOD (biological oxygen demand), and high phenol content or phenoxyalcohol content etc. This suppresses the burden on the environment. The phenol or phenoxyalcohol remaining in a precipitating step is not preferable, because the remaining phenol or phenoxyalcohol may cause a deterioration in hue of the finished product.

In a case where an unreacted phenol or unreacted phenoxyalcohol is distilled away from the reaction mixture liquid and the reaction mixture liquid is concentrated without adding an alkali, a remaining catalyst and/or eluate of the catalyst accelerates generation of by-products, and thus causes deteriorations in purity and hue, and a reduction in yield. Note however that, according to the present invention, since an alkali is added as described earlier, it is possible, by concentrating the reaction mixture liquid by heat, to distill away and recover an unreacted phenol or unreacted phenoxyalcohol without reducing purity and yield of the finished products. Also in a case where the catalyst is separated from the reaction mixture liquid after the reaction or a case where a continuous reaction is carried out by using a catalyst-filled apparatus, addition of an alkali makes it possible to obtain a finished product that has better hue, purity and yield.

(ii-3) Extracting Step

In the extracting step, subsequently, an extract agent constituted by water and an organic solvent separable from water is added to the concentrated liquid obtained in the concentrating step. Thereby, a fluorene derivative serving as a target substance, which is for example 9,9-bis(4-(2-hydroxyethoxy) phenyl)fluorene, is partitioned into an organic phase. Thereafter, an aqueous phase is separated.

The step of extracting the fluorene derivative is carried out by a usual method. Specifically, the step is carried out by (a)

adding water and an organic solvent separable from water to the concentrated liquid, (b) heating the mixture liquid to preferably a raised temperature, specifically a temperature at which the organic phase becomes uniform, under stirring if needed, and (c) partitioning the fluorene derivative into the organic phase by stirring. In this method, the water and the organic solvent separable from water may be added simultaneously or one of them may be added first and the other may be added thereafter.

The phenol or phenoxyalcohol such as phenoxyethanol, which is high in water solubility, has been removed in the concentrating step. Therefore, the amount of the organic solvent to be used in the extracting step can be reduced as compared to a case where the extraction is carried out in the presence of the phenol or phenoxyalcohol. Further, liquid separability is improvised, and thus a finished product with higher purity can be obtained. Moreover, TOC, COD, BOD and phenol content in waste water are reduced as compared to the case where the extraction is carried out in the presence of the phenol or phenoxyalcohol. This makes it possible to reduce the burden on the environment.

The water for use in the extracting step is for example, but not limited to, industrial water, tap water, ion exchange water, or distilled water. It is preferable to use ion exchange water or distilled water, because use of such water will reduce minute impurities in the finished product.

A mixture liquid obtained by adding the extract agent and partitioning the fluorene derivative into the organic phase is allowed to stand, and thereafter is subjected to liquid separation to separate the aqueous solution. To an obtained organic phase, further water can be added, and thereafter the organic phase can be washed two or more times by the same operations.

(ii-4) Precipitating and Filtering Step

In the precipitating and filtering step, subsequently, the organic phase obtained in the extracting step is cooled, thereby crystals of the fluorene derivative are precipitated. Thereafter, the crystals are recovered by filtration.

Note here that the crystallization can be carried out after dehydrating the organic phase by removing water from the organic phase. How to dehydrate the organic phase is for example, but not limited to, dehydrating by adding a dehydrating agent, dehydrating under reduced pressure, or azeotropic dehydration with a solvent. In a case where the organic phase is not uniform or a case where crystals are already precipitated, the crystallization can be carried out after dissolving the organic phase by heat. A temperature at which to dissolve the organic phase by heat is not particularly limited. The temperature is preferably not less than 55° C. but not more than a boiling point of a solvent to be used, more preferably 60° C. to 150° C., and further preferably 70° C. to 110° C. If the crystallization is carried out when the organic phase is not sufficiently dissolved due to low temperatures, the finished product may be inferior in purity or hue. Further, it may be impossible to achieve a uniform crystal form that is excellent as a resin material.

A temperature at which crystals of the fluorene derivative are to be precipitated is not particularly limited. In order to obtain a uniform crystal form excellent as a resin material, the crystals of the fluorene derivative are caused to start to precipitate at a temperature of not less than 50° C. but less than the boiling point of the solvent (preferably 60° C. to 100° C., and more preferably 70° C. to 90° C.). After the crystals are caused to start to precipitate at a temperature of not less than 50° C., the mixture may be further cooled. A temperature at which the cooling is finished is not particularly limited. Usually, the temperature is −20° C. to 50° C., preferably 0° C. to 40° C., and further preferably 10° C. to 30° C. If this temperature is low, purity tends to decrease. If this temperature is high, more crystals are lost in the solvent and economical efficiency and productivity are reduced. The cooling rate is not particularly limited. Usually, the cooling rate is 0.01 to 2° C./min, and preferably 0.1 to 0.5° C./min. During cooling, it is preferable that crystals of the fluorene derivative be added as seed crystals to the mixture. How to add the seed crystals is not particularly limited. Usually, the seed crystals are added for example at a temperature of 1° C. to 10° C. below, and preferably at a temperature of 1° C. to 3° C. below the temperature at which the fluorene derivative is saturated and dissolved. That is, usually, the seed crystals are added at a temperature falling within the metastable range. The amount of the seed crystals to be added is 0.01 wt % to 10 wt %, preferably 0.05 wt % to 5 wt %, and further preferably 0.1 wt % to 2 wt %, relative to the fluorenone used.

The crystals thus precipitated are recovered by filtration. Obtained crystals may be washed with a used solvent etc. and/or dried. The crystals of the fluorene derivative obtained in this manner show high purity and good hue, and therefore are excellent as a resin material. The crystallization operation can be carried out two or more times if needed. Note however that, according to the present invention, it is possible to obtain a high-purity fluorene derivative having good hue by a single crystallization operation.

(ii-5) Step of Recycling Phenol or Phenoxyalcohol

Further, an unreacted compound of formula (I), which was separated in the concentrating step, is preferably recycled to the reacting step to be reused as a raw material.

According to the present invention, at least part of, preferably 50% to 100% of, and particularly preferably all of the phenol or phenoxyalcohol recovered in the concentrating step are recycled as a raw material to the reacting step without being subjected to any special process. The phenol or phenoxyalcohol recovered in the present invention usually shows purity of 99% or more, and has no or little accumulation of impurities such as by-products or degradation products. Therefore, the phenol or phenoxyalcohol can be recycled to be reused.

According to the present invention, an excess phenol or excess phenoxyalcohol, which is used for the purpose of improving yield and reaction efficiency, can be reused by simple operations without wasting. This makes it possible to produce a fluorene derivative such as 9,9-bis(4-(2-hydroxyethoxy)phenyl)fluorene in an economically advantageous manner. Further, this reduces wastes, thereby reducing the burden on the environment.

According to the method for producing the fluorene derivative in accordance with the present invention, the configurations described in the (i) and (ii-1) to (ii-5) can be suitably combined within the matters described therein. Accordingly, the method for producing the fluorene derivative in accordance with the present invention also encompasses a method for producing 9,9-bis(4-(2-hydroxyethoxy)phenyl)fluorene, the method including the steps of:

(a) reacting fluorenone with phenoxyethanol in the presence of an acid catalyst under reduced pressure to obtain a reaction mixture liquid containing 9,9-bis(4-(2-hydroxyethoxy)phenyl)fluorene;

(b) after addition of an alkali to a reaction mixture liquid thus obtained, concentrating the reaction mixture liquid by heat to obtain a concentrated liquid and to separate and recover an unreacted phenoxyethanol;

(c) recycling a separated and recovered phenoxyethanol to the step (a) so that the separated and recovered phenoxyethanol is reused as a raw material;

(d) extracting the 9,9-bis(4-(2-hydroxyethoxy)phenyl)fluorene by adding an extract agent constituted by water and an organic solvent separable from water to the concentrated liquid to partition the 9,9-bis(4-(2-hydroxyethoxy)phenyl) fluorene into an organic phase, and thereafter separating an aqueous phase; and (e) precipitating crystals of the 9,9-bis(4-(2-hydroxyethoxy)phenyl)fluorene by cooling the organic phase, and thereafter filtering the organic phase to recover the crystals. Needless to say, the present invention encompasses also a method for producing a fluorene derivative in which method the phenoxyethanol of the above steps (a) through (e) is replaced by a compound of formula (I).

(iii)

The following description discusses another embodiment of the present invention in detail. Note, however, that the present embodiment is not limited to the following description.

The inventors of the present invention described earlier (a) a method for producing 9,9-bis(4-(2-hydroxyethoxy)phenyl) fluorene from fluorenone and 2-phenoxyethanol in the presence of a heteropoly acid catalyst (this method is described in Patent Literature 11) and (b) a method for producing 9,9-bis (4-(2-hydroxyethoxy)phenyl)fluorene with a melting point of 160° C. to 166° C. (this method is described in Patent Literature 12). By these methods, it is possible to obtain 9,9-bis(4-(2-hydroxyethoxy)phenyl)fluorene that keeps certain quality and is excellent as a polymer material, because no sulfur is to be mixed in. Note however that, in order to produce the 9,9-bis(4-(2-hydroxyethoxy)phenyl)fluorene in an economically efficient and industrially advantageous manner, it is necessary to simplify a purification operation by reducing reaction time and suppressing generation of by-products.

In view of this, another object of the present invention is to provide a method for producing 9,9-bis(4-(2-hydroxyethoxy) phenyl)fluorene, which method is suitable for industrial use and is economically advantageous. That is, another object of the present invention is to provide a method for quickly and efficiently producing 9,9-bis(4-(2-hydroxyethoxy)phenyl) fluorene that keeps constant quality and is excellent as a polymer material, while suppressing generation of by-products.

The inventors of the present invention diligently studied to attain the above object. As a result, the inventors have found that, by reacting fluorenone with 2-phenoxyethanol in the presence of an acid catalyst at a temperature falling within a certain range under reduced pressure, it is possible to produce 9,9-bis(4-(2-hydroxyethoxy)phenyl)fluorene excellent as a polymer material in an economically advantageous manner. This is because, by reacting fluorenone with 2-phenoxyethanol in the presence of an acid catalyst at a temperature falling within a certain range under reduced pressure, it is possible to reduce the reaction time and suppress generation of by-products (particularly multimers of 9,9-bis(4-(2-hydroxyethoxy) phenyl)fluorene), and thus the purification operation is simplified.

According to the present embodiment, it is possible to provide a method for producing 9,9-bis(4-(2-hydroxyethoxy) phenyl)fluorene by reacting fluorenone with 2-phenoxyethanol in the presence of an acid catalyst, which method is for producing 9,9-bis(4-(2-hydroxyethoxy)phenyl)fluorene containing no sulfur and being excellent as a polymer material in an economically efficient and industrially advantageous manner.

According to the present embodiment, fluorenone is reacted with 2-phenoxyethanol with use of an acid catalyst under a certain dehydrated condition where pressure is reduced, to obtain 9,9-bis(4-(2-hydroxyethoxy)phenyl)fluorene. The other reaction conditions are not particularly limited. Usually, the reaction is carried out by (a) feeding fluorenone, 2-phenoxyethanol, and an acid catalyst into a reaction apparatus and (b) heating and stirring a mixture in air or under inert gas atmosphere such as nitrogen or helium. The reaction may be carried out batchwise or continuously.

The reaction temperature in the present embodiment varies depending on the amount of 2-phenoxyethanol to be used, the type of acid catalyst, and degree of pressure reduction. The reaction temperature is preferably 30° C. to 150° C., more preferably 90° C. to 150° C., further preferably 100° C. to 140° C., and particularly preferably 120° C. to 140° C. Reaction temperatures of not more than 150° C. suppress an increase in by-products and thus improve purity and yield. Further, the reaction temperatures of not more than 150° C. prevent coloration of the finished product. Therefore, the reaction temperatures of not more than 150° C. are preferred. Temperatures of not less than 30° C. are preferred because, at such temperatures, the reaction proceeds in a favorable manner and time taken for completion of the reaction is not too long. In a case where a heteropoly acid is used as an acid catalyst, the reaction temperature in the present embodiment is more preferably 90° C. to 150° C.

The reduced pressure in the present embodiment is preferably not more than $39 \times 10^3$ Pa, more preferably not more than $14 \times 10^3$ Pa, further preferably not more than $6.7 \times 10^3$ Pa, and particularly preferably $4.0 \times 10^3$ Pa to $0.3 \times 10^3$ Pa. The reduced pressure of not more than $39 \times 10^3$ Pa is preferred, because the reaction proceeds in a favorable manner or time taken for completion of the reaction is not too long even at reaction temperatures of not more than 150° C. In a case of a reflux dehydration reaction using an azeotropic dehydration solvent, the reaction may proceed at normal pressures at temperatures of not more than 150° C. Note, however, that the reduced pressure of not more than $39 \times 10^3$ Pa is preferred because time taken for completion of the reaction is not too long. Meanwhile, as the reaction scale increases, the reaction time tends to increases. Also in this regard, the above reduced pressure is preferred because the time taken for completion of the reaction is not too long and therefore the content of multimers is not too large. According to the method of the present embodiment, the reaction time is reduced. In addition, the method of the present embodiment is largely unaffected by equipment and fate reaction scale, and is capable of suppressing generation of multimers. This simplifies the purification. In a case where a heteropoly acid is used as an acid catalyst, the reduced pressure in the present embodiment is more preferably not more than $14 \times 10^3$ Pa.

As the acid catalyst for use in the present embodiment, the acid catalysts described in the above (i) can be suitably used. Among those, a heteropoly acid and ion exchange resin are more preferred because (a) such catalysts can be separated from a reaction mixture liquid after completion of the reaction by a simple operation such as filtration and (b) a continuous reaction is available by using a flowing reaction apparatus filled with such catalysts. Further, a heteropoly acid is particularly preferred among the above, because fewer components are eluted therefrom and a higher-purity target substance with better hue can be obtained.

The heteropoly acid is a general term indicative of a compound made from two or more different inorganic oxyacids which are combined by condensation. Various heteropoly acids can be obtained by changing the combination of (a) an oxyacid at the center and (b) another oxyacid to be combined with the above oxyacid by condensation. A small number of element(s) that form(s) the oxyacid at the center is called a hetero element. An element(s) that form(s) the oxyacid to be combined with the oxyacid at the center by condensation is called a poly element. The poly element(s) may be of the same kind or may be of two or more kinds.

The hetero element of the oxyacid that forms the heteropoly acid is not particularly limited. Examples of the hetero element include: copper, beryllium, boron, aluminium, carbon, silicon, germanium, tin, titanium, zirconium, cerium, thorium, nitrogen, phosphorus, arsenic, antimony, vanadium, niobium, tantalum, chromium, molybdenum, tungsten, uranium, selenium, tellurium, manganese, iodine, iron, cobalt, nickel, rhodium, osmium, iridium, and platinum. Phosphorus or silicon is preferred. Further, the poly element of the oxyacid that forms the heteropoly acid is for example, but not limited to, vanadium, molybdenum, tungsten, niobium, or tantalum. Vanadium, molybdenum, or tungsten is preferred.

As a heteropoly acid anion that forms a heteropoly acid backbone, anions of various compositions can be used. Examples of composition of such anion include $XM_{12}O_{40}$, $XM_{12}O_{42}$, $XM_{18}O_{62}$, and $XM_6O_{24}$. Preferred composition of such heteropoly acid anion is $XM_{12}O_{40}$. In each formula, X is a hetero element and M is a poly element. Specific examples of a heteropoly acid having the above composition include: molybdophosphoric acid, tungstophosphoric acid, molybdosilicic acid, tungstosilicic acid, and molybdo vanado phosphoric acid.

The heteropoly acid may be a free heteropoly acid. Further, salt of the heteropoly acid, which salt is obtained by replacing part or all of protons by other cation(s), can be used. Therefore, in the present embodiment, the term "heteropoly acid" encompasses also salt of the heteropoly acid. Examples of the cation that can replace the proton include ammonium ions, alkali metal ions, and alkaline earth metal ions.

The heteropoly acid may be an anhydrous or may contain water of crystallization. Note, however, that the heteropoly acid is preferably anhydrous, because the reaction proceeds more quickly and generation of by-products is suppressed. In a case where the heteropoly acid contains water of crystallization, the heteropoly acid can be subjected to a dehydration process such as drying under reduced pressure or azeotropic dehydration with a solvent, beforehand. This makes it possible to achieve an effect same as in the case where the heteropoly acid is anhydrous. The heteropoly acid may be supported on a carrier such as activated carbon, alumina, silica-alumina, or diatom earth. These heteropoly acids may be used independently or two or more heteropoly acids can be used in combination. Further, another catalyst other than the heteropoly acid can be used together with the heteropoly acid as needed, provided that the object of the present invention is attained.

The amount of the heteropoly acid to be used is not particularly limited. In order to achieve a sufficient rate of reaction, the amount is not less than 0.0001 times by weight, preferably 0.001 to 30 times by weight, and further preferably 0.01 to 5 times by weight, relative to fluorenone.

The amount of 2-phenoxyethanol to be used in the present embodiment is not particularly limited. In view of side reaction inhibition and economical efficiency, usually, the amount is 2 mol to 50 mol, preferably 2.5 mol to 20 mol, and further preferably 3 mol to 10 mol, relative to 1 mol of fluorenone. In a case where 2-phenoxyethanol is distilled out of the reaction system during reaction under reduced pressure, the 2-phenoxyethanol thus distilled may be directly removed out of the reaction system. Alternatively, the 2-phenoxyethanol can be separated from distilled water and then fed back into the reaction system.

In the present embodiment, the reaction can be carried out under reduced pressure in the presence of a solvent as needed, provided that the object of the present invention is attained. The solvent that may be present together with the fluorenone and 2-phenoxyethanol is not particularly limited. Examples of such a solvent include: aromatic hydrocarbon solvents such as toluene and xylene; halogenated aromatic hydrocarbon solvents such as chlorobenzene and dichlorobenzene; aliphatic hydrocarbon solvents such as pentane, hexane, and heptane; halogenated aliphatic hydrocarbon solvents such as dichloromethane and 1,2-dichloroethane; aliphatic ether solvents and cyclic ether solvents such as diethyl ether, di-isopropyl ether, methyl-t-butyl ether, diphenyl ether, tetrahydrofuran, and dioxane; ester solvents such as ethyl acetate and butyl acetate; nitrile solvents such as acetonitrile, propionitrile, butyronitrile, and benzonitrile; and amide solvents such as N,N-dimethylformamide, N,N-dimethylacetamide, and 1-methyl-2-pyrrolidinone. The solvent that may be present together with the fluorenone and 2-phenoxyethanol is more preferably an aromatic hydrocarbon solvent or a halogenated aromatic hydrocarbon solvent, and further preferably toluene, xylene, chlorobenzene, or dichlorobenzene.

An obtained reaction mixture liquid contains not only 9,9-bis(4-(2-hydroxyethoxy)phenyl)fluorene (i.e., target substance), unreacted 2-phenoxyethanol and the catalyst, but also by-products such as an isomer of the 9,9-bis(4-(2-hydroxyethoxy)phenyl)fluorene, and a dimer, trimer, bisphenol, and trisphenol etc. (hereinafter collectively referred to as multimers) of 9,9-bis(4-(2-hydroxyethoxy)phenyl)fluorene.

After the reaction, the obtained reaction mixture may be directly subjected to cooling crystallization so as to precipitate the 9,9-bis(4-(2-hydroxyethoxy)phenyl)fluorene. Note however that, usually, the reaction mixture is subjected to aftertreatment such as wash, concentration or dilution, and thereafter is subjected to cooling crystallization so as to precipitate the 9,9-bis(4-(2-hydroxyethoxy)phenyl)fluorene. Note here that, if a lot of by-products (particularly a lot of multimers) are present in the reaction mixture, usually, a temperature at which crystals start to precipitate is lower than 50° C., and obtained crystals usually have a melting point of 100° C. to 130° C. Therefore, in order to obtain crystals of the 9,9-bis(4-(2-hydroxyethoxy)phenyl)fluorene, which crystals has a melting point of 160° C. to 166° C. and is excellent as a polymer material, it is necessary to repeat the purification. According to the method of the present embodiment, since the content of multimers in the reaction mixture is small, it is necessary to carry out only a single crystallization operation to recover the 9,9-bis(4-(2-hydroxyethoxy)phenyl)fluorene in the form of crystals having a melting point of 160° C. to 166° C.

The purification of the present embodiment is carried out by (a) dissolving the reaction mixture into at least one solvent selected from the group consisting of aromatic hydrocarbon solvents, ketone solvents and ester solvents at a temperature of more than 50° C., and thereafter (b) cooling an obtained mixture to cause crystals of the 9,9-bis(4-(2-hydroxyethoxy)phenyl)fluorene to start to precipitate out at a temperature of not less than 50° C. but less than a boiling point of a solvent (preferably 60° C. to 100° C., more preferably 70° C. to 90° C.). The temperature at which the reaction mixture is dissolved is not particularly limited, but is preferably not less than 55° C. but not more than a boiling point of a solvent to be used, more preferably 60° C. to 150° C., and further preferably 70° C. to 110° C. If this temperature is low, it may be impossible to obtain a substantially uniform crystal form. After the crystals are caused to start to precipitate at a temperature of not less than 50° C., the mixture may be further cooled. A temperature at which the cooling is finished is not particularly limited. Usually, the temperature is −20° C. to 50° C., preferably 0° C. to 40° C., and further preferably 10° C. to 30° C. If this temperature is low, purity tends to decrease. If this temperature is high, more crystals are lost in the solvent and economical efficiency and productivity are reduced. The cooling rate is not particularly limited. Usually, the cooling rate is 0.01 to 2° C./min, and preferably 0.1 to 0.5° C./min. During cooling, it is preferable that crystals of the 9,9-bis(4-(2-hydroxyethoxy)phenyl)fluorene be added as seed crystals to the mixture. How to add the seed crystals is not particularly limited. Usually, the seed crystals having a melting point of 160° C. to 166° C. are added for example at a temperature of 1° C. to 10° C. below, and preferably at a temperature of 1° C. to 3° C. below the temperature at which the 9,9-bis(4-(2-hydroxyethoxy)phenyl)fluorene is saturated and dissolved. That is, usually, the seed crystals having a melting point of 160° C. to 166° C. are added at a temperature falling within the metastable range. The mount of the seed crystals to be added is 0.01 wt % to 10 wt %, preferably 0.05 wt % to 5 wt %, and further preferably 0.1 wt % to 2 wt %, relative to the fluorenone used.

The crystals thus precipitated are recovered by filtration etc. Obtained crystals may be washed with a used solvent etc. and/or dried. The crystals of the 9,9-bis(4-(2-hydroxyethoxy)phenyl)fluorene obtained in this manner have a melting point of 160° C. to 166° C., and therefore is excellent as a resin material.

EXAMPLES

The following description discusses examples of the present invention. Note, however, that the present invention is not limited to the examples.

In the examples, the amount of remaining fluorenone, purity of a fluorene derivative, and content of multimers of the fluorene derivative are determined by liquid chromatography (LC-2010C manufactured by Shimadzu Corporation.) using a reverse phase column (5 μm, 4.6 mm in diameter×150 mm) at a wavelength of 254 nm, and are presented in area percentage.

Phenol content in waste water is determined by the 4-aminoantipyrine (AP) method of JIS K0102 28.1.

A melting point is a temperature at the melting endothermic peak of the differential scanning calorie (DSC) determined with use of a differential scanning calorimeter (manufactured by SEICO Electronics Industrial Co., Ltd.) under the following conditions.
Differential Scanning Calories (Dsc) Measurement Conditions:
Reagent: Aluminium oxide
Heating rate: 10° C./min
Test range: 40° C. to 260° C.
Atmosphere: Open, Nitrogen 40 ml/min

Example 1

A reaction was carried out by (a) feeding 40.0 g of fluorenone, 306.7 g of 2-phenoxyethanol, 160 g of toluene, and 1.0 g of tungstophosphoric acid into a 500 ml glass reactor vessel equipped with a stirrer, a condenser and a thermometer, and (b) stirring a mixture under toluene reflux for 8 hours. The amount of remaining fluorenone was determined by HPLC, and found to be 0.1% or less. To an obtained reaction mixture liquid, 1.0 g of 29% sodium hydroxide aqueous solution was added, and thereafter toluene and 240.0 g of 2-phenoxyethanol were distilled away by concentration under reduced pressure. To an obtained concentrated liquid, 280 g of toluene and 60 g of water were added, and the mixture liquid was stirred at 80° C. Thereafter, an aqueous phase was separated and removed, and a target substance partitioned in an organic phase was recovered. A separated waste water was analyzed, and it was found that a total organic carbon (hereinafter referred to as TOC)=850 mg/L, chemical oxygen demand (hereinafter referred to as COD)=2500 mg/L, biological oxygen demand (hereinafter referred to as BOD)=200 mg/L, and phenol content=0.1 mg/L or less.

An obtained organic phase was washed twice with 60 g of water and thereafter cooled to 20° C. Then, precipitated crystals were subjected to filtration and drying to obtain 76.8 g of 9,9-bis(4-(2-hydroxyethoxy)phenyl)fluorene (yield: 78.8%, LC purity: 98.2%). Obtained 9,9-bis(4-(2-hydroxyethoxy)phenyl)fluorene was dissolved by heat at 230° C. for 2 hours. The 9,9-bis(4-(2-hydroxyethoxy)phenyl)fluorene thus dissolved show a hue of 100 in APHA. The total amount of toluene used in the production was 5.7 parts by weight relative to 1 part by weight of the 9,9-bis(4-(2-hydroxyethoxy)phenyl)fluorene.

Example 2

The same operations as in Example 1 were repeated except that, after the reaction was carried out in the same manner as in Example 1, 0.9 g of 50% potassium hydroxide aqueous solution was added to an obtained reaction mixture liquid instead of 1.0 g of 29% sodium hydroxide aqueous solution. In this way, 76.5 g of 9,9-bis(4-(2-hydroxyethoxy)phenyl) fluorene (yield: 78.5%, LC purity 98.5%) was obtained. Obtained 9,9-bis(4-(2-hydroxyethoxy)phenyl)fluorene was dissolved by heat at 230° C. for 2 hours. The 9,9-bis(4-(2-hydroxyethoxy)phenyl)fluorene thus dissolved show a hue of 100 in APHA. A separated waste water was analyzed, and it was found that TOC=920 mg/L, COD=3100 mg/L, BOD=250 mg/L, and phenol content=0.1 mg/L or less.

Comparative Example 1

A reaction was carried out in the same manner as in Example 1. Thereafter, 280 g of toluene, 80 g of water, and 1.4 g of 29% sodium hydroxide aqueous solution were added to an obtained reaction mixture liquid, and the reaction mixture liquid was neutralized by stirring at 80° C. Thereafter, an aqueous phase was separated and removed. A separated waste water was analyzed, and it was found that TOC=11000 mg/L, COD=32000 mg/L, BOD=2300 mg/L, and phenol content=830 mg/L.

An organic phase was further washed twice with 80 g of water, and thereafter toluene and 220.0 g of 2-phenoxyethanol were distilled away from the organic phase by concentration under reduced pressure. To an obtained concentrated liquid, 280 g of toluene was added, and the mixture liquid was cooled to 20° C. Then, precipitated crystals were subjected to filtration and drying to obtain 73.0 g of 9,9-bis(4-(2-hydroxyethoxy)phenyl)fluorene (yield: 75.0%, LC purity: 97.7%). Obtained 9,9-bis(4-(2-hydroxyethoxy)phenyl)fluorene was dissolved by heat at 230° C. for 2 hours. The 9,9-bis(4-(2-hydroxyethoxy)phenyl)fluorene thus dissolved show a hue of 160 in APHA. The total amount of toluene used in the production was 9.9 parts by weight relative to 1 part by weight of the 9,9-bis(4-(2-hydroxyethoxy)phenyl)fluorene.

Comparative Example 2

A reaction was carried out in the same manner as in Example 1. Thereafter, toluene and 2-phenoxyethanol were recovered by concentration under reduced pressure with no alkali added to an obtained mixture liquid. An obtained concentrated liquid was subjected to the same operations as in Example 1 to obtain 71.6 g of 9,9-bis(4-(2-hydroxyethoxy) phenyl)fluorene (yield: 73.5%, LC purity: 95.3%). Obtained 9,9-bis(4-(2-hydroxyethoxy)phenyl)fluorene was dissolved by heat at 230° C. for 2 hours. The 9,9-bis(4-(2-hydroxyethoxy)phenyl)fluorene thus dissolved show a hue of 200 or greater in APHA, and was cloudy.

Example 3

A reaction was carried out by (a) feeding 23 g of fluorenone, 1.3 g of dodecyl mercaptan, and 161.0 g of 2-methyl phenol into a 500 ml glass reactor vessel equipped with a stirrer, a condenser and a thermometer, (b) dropping 13.0 g of 35% hydrochloric acid to a mixture, and (c) stirring the mixture at 50° C. for 2 hours. The amount of remaining fluorenone was determined by HPLC, and found to be 0.1% or less. To an obtained reaction mixture liquid, 18.5 g of 29% sodium hydroxide aqueous solution was added, and thereafter 94.0 g of 2-methyl phenol was distilled away from an organic phase by concentration under reduced pressure. To an obtained concentrated liquid, 161 g of toluene and 23 g of water were added, and the mixture liquid was stirred at 80° C. Thereafter, an aqueous phase was separated and removed, and a target substance partitioned in the organic phase was recovered. The organic phase was further washed twice with 23 g of water, and cooled to 10° C. Then, precipitated crystals were subjected to filtration and drying to obtain 37.9 g of 9,9-bis(4-hydroxy-3-methylphenyl)fluorene (yield: 84.3%, LC purity: 99.3%). Obtained 9,9-bis(4-hydroxy-3-methylphenyl)fluorene was dissolved by heat at 230° C. for 2 hours. The 9,9-bis(4-hydroxy-3-methylphenyl)fluorene thus dissolved had a hue of 1 in Gardner. The total amount of toluene used in the production was 4.2 parts by weight relative to 1 part by weight of the 9,9-bis(4-hydroxy-3-methylphenyl)fluorene.

Example 4

A reaction was carried out by (a) feeding 23.0 g of fluorenone, 0.4 g of dodecyl mercaptan, 276.0 g of 2-methyl phenol, and 17.5 g of Nafion (registered trademark) NR50 (perfluorosulfonic acid cation-exchange resin manufactured by DuPont) into a 500 ml glass reactor vessel equipped with a stirrer, a condenser and a thermometer, and (b) stirring a mixture at 95° C. for 8 hours. The amount of remaining fluorenone was determined by HPLC, and found to be 0.1% or less. The ion exchange resin was removed by filtration to obtain a reaction mixture liquid. To the reaction mixture liquid thus obtained, 0.5 g of 29% sodium hydroxide aqueous solution was added, and thereafter 95.0 g of 2-methyl phenol was distilled away from an organic phase by concentration under reduced pressure. To an obtained concentrated liquid, 161 g of toluene and 23 g of water were added, and the mixture liquid was stirred at 80° C. Thereafter, an aqueous phase was separated and removed, and a target substance partitioned in the organic phase was recovered. The organic phase was further washed twice with 23 g of water, and cooled to 10° C. Then, precipitated crystals were subjected to filtration and drying to obtain 38.5 g of 9,9-bis(4-hydroxy-3-methylphenyl)fluorene (yield: 85.7%, LC purity: 99.5%). Obtained 9,9-bis(4-hydroxy-3-methylphenyl)fluorene was dissolved by heat at 230° C. for 2 hours. The 9,9-bis(4-hydroxy-3-methylphenyl)fluorene thus dissolved show a hue of 2 in Gardner. The total amount of toluene used in the production was 4.2 parts by weight relative to 1 part by weight of the 9,9-bis(4-hydroxy-3-methylphenyl)fluorene.

Comparative Example 3

A reaction was carried out in the same manner as in Example 3. To an obtained reaction mixture liquid, 135 g of toluene, 23 g of water, and 17.9 g of 29% sodium hydroxide aqueous solution were added, and the reaction mixture liquid was neutralized by stirring at 80° C. Thereafter, an aqueous phase was separated and removed. An organic phase was further washed twice with 23 g of water. From the organic phase, toluene and 91.5 g of 2-methyl phenol were distilled away by concentration under reduced pressure. Thereafter, 161 g of toluene was added to a concentrated liquid, and the mixture liquid was cooled to 10° C. Then, precipitated crystals were subjected to filtration and drying to obtain 37.0 g of 9,9-bis(4-hydroxy-3-methylphenyl)fluorene (yield: 82.5%, LC purity: 98.7%). Obtained 9,9-bis(4-hydroxy-3-methylphenyl)fluorene was dissolved by heat at 230° C. for 2 hours. The 9,9-bis(4-hydroxy-3-methylphenyl)fluorene thus dissolved show a hue of 4 in Gardner. The total amount of toluene used in the production was 8 parts by weight relative to 1 part by weight of the 9,9-bis(4-hydroxy-3-methylphenyl)fluorene.

Example 5

A reaction was carried out by (a) adding 50.0 g (0.28 mol) of fluorenone, 1.2 g of tungstophosphoric acid, 83.0 g (0.60 mol) of phenoxyethanol, and 300 g (2.17 mol) of phenoxyethanol recovered in the concentrating step to a glass reactor vessel equipped with a stirrer, a nitrogen-blowing tube, a thermometer and a reflux condenser, (b) gradually heating a mixture to 130° C. under a reduced pressure of $2.0 \times 10^3$ Pa, and thereafter (c) stirring the mixture under a reduced pressure between $2.0 \times 10^3$ and $3.0 \times 10^3$ Pa for 4 hours at a temperature between 130° C. and 135° C. while removing generated water out of the reaction system. A reaction liquid was subjected to liquid chromatography, and found to have 0.3% or less of remaining fluorenone (reacting step).

An obtained reaction mixture liquid was cooled to 80° C., and 0.9 g of 29% sodium hydroxide aqueous solution was added to the reaction mixture liquid. The reaction mixture liquid was stirred for 1 hour, and thereafter subjected to concentration under reduced pressure while being gradually heated to 150° C. In this way, 300 g of phenoxyethanol was distilled away. The phenoxyethanol thus recovered was analyzed by gas chromatography, and found to be 99.8% (concentrating step).

An obtained concentrated liquid was cooled, and 300 g of toluene and 70 g of ion exchange water were added to the concentrated liquid. The mixture liquid was stirred at 80° C. for 30 minutes, thereby a target substance was partitioned into an organic phase. An obtained solution was allowed to stand for 30 minutes, and thereafter an aqueous phase was separated and removed. Then, the organic phase was recovered. The organic phase thus obtained was further washed twice with 60 g of ion exchange water (extracting step).

The organic phase thus obtained was heated to 110° C. and stirred for 1 hour. During heating and stirring, water distilled out of the system was separated and removed with use of an oily water separator. Next, the organic phase thus obtained was confirmed to be uniform, and thereafter was cooled to 65° C. To this solution, 0.2 g of crystals of 9,9-bis(4-(2-hydroxyethoxy)phenyl)fluorene were added as seed crystals, and incubated at 65° C. for 2 hours. It was confirmed that crystals were precipitated. Then, the solution was cooled to 25° C., and precipitated crystals were subjected to centrifugal filtration (precipitating and filtering step).

The crystals were dried under reduced pressure, thereby a solvent was removed. In this way, 107.8 g of white crystals of 9,9-bis(4-(2-hydroxyethoxy)phenyl)fluorene were obtained. The product yield relative to a raw material, i.e., fluorenone, was 88.6%, and purity was 99.0%. Further, the 9,9-bis(4-(2-hydroxyethoxy)phenyl)fluorene was dissolved by heat at 230° C. for 2 hours. The 9,9-bis(4-(2-hydroxyethoxy)phenyl) fluorene thus dissolved show a melt hue of 40 in APHA. Transmittance of the 9,9-bis(4-(2-hydroxyethoxy)phenyl) fluorene in a dioxan solvent at 400 nm was 99.5%. Minute impurities in the crystals included 5 ppb of sodium, 7 ppb of iron (ICP-MS method), and 0.1 ppm or less of sulfur (ion chromatography).

In generated waste water, COD=3000 mg/L, BOD=220 mg/L, phenol content=0.1 mg/L or less. The total amount of toluene used in the production was 300 g (2.8 parts by weight relative to 1 part by weight of the finished product).

Comparative Example 4

A reaction was carried out by (a) feeding 50.0 g of fluorenone, 383 g of phenoxyethanol, 200 g of toluene, and 1.2 g of tungstophosphoric acid into a glass reactor vessel equipped with a stirrer, a nitrogen-blowing tube, thermometer and a reflux condenser, and (b) stirring a mixture for 12 hours under toluene reflux while removing generated water out of the reaction system. To an obtained reaction mixture liquid, 350 g of toluene, 100 g of ion exchange water, and 1.8 g of 29% sodium hydroxide aqueous solution were added, and the reaction mixture was stirred at 80° C. for 30 minutes. This solution was allowed to stand for 30 minutes, and thereafter an aqueous phase was separated and removed. Then, an organic phase was recovered. The organic phase thus obtained was further washed twice with 60 g of ion exchange water. The organic phase was subjected to concentration under reduced pressure, thereby toluene and phenoxyethanol where distilled away. The phenoxyethanol thus recovered was analyzed by gas chromatography, and found to be 98.3%. To an obtained concentrated liquid, 300 g of toluene was added, and the mixture liquid was cooled to 20° C. Then, precipitated crystals were subjected to filtration and drying to obtain 92.0 g of 9,9-bis(4-(2-hydroxyethoxy)phenyl)fluorene. The product yield relative to the raw material, i.e., fluorenone, was 75.6%, and purity was 97.5%. Further, the 9,9-bis(4-(2-hydroxyethoxy)phenyl)fluorene was dissolved by heat at 230° C. for 2 hours. The 9,9-bis(4-(2-hydroxyethoxy)phenyl)fluorene thus dissolved show a hue of 140 in APHA. Transmittance of the 9,9-bis(4-(2-hydroxyethoxy)phenyl)fluorene in a dioxan solvent at 400 nm was 98.3%.

In generated waste water, COD=30000 mg/L, BOD=4200 mg/L, and phenol content=160 mg/L. The total amount of toluene used in the production was 850 g (9.2 parts by weight relative to 1 part by weight of the finished product).

Example 6

A reaction was carried out by (a) feeding 23 g of fluorenone, 0.57 g of tungstophosphoric acid, and 161 g of 2-methyl phenol into a 500 ml glass reactor vessel equipped with a stirrer, a condenser and a thermometer, and (b) stirring a mixture under a reduced pressure of $1.3 \times 10^3$ Pa at 70° C. for 4 hours while removing generated water out of the system. The amount of remaining fluorenone was determined by HPLC, and found to be 0.1% or less. To an obtained reaction mixture liquid, 0.6 g of 29% sodium hydroxide aqueous solution was added, and 103.5 g of 2-methyl phenol was recovered from an organic phase by concentration under reduced pressure. To a concentrated liquid, 161 g of toluene and 46 g of water were added, and the mixture liquid was stirred at 80° C. Thereafter, an aqueous phase was separated and removed, and a target substance partitioned in an organic phase was recovered. The organic phase was further washed twice with 46 g of water, and cooled to 10° C. Then, precipitated crystals were subjected to filtration and drying to obtain 40.3 g of 9,9-bis(4-hydroxy-3-methylphenyl)fluorene (yield: 83.5%, LC purity: 99.3%). Obtained 9,9-bis(4-hydroxy-3-methylphenyl)fluorene was dissolved by heat at 230° C. for 2 hours. The 9,9-bis(4-hydroxy-3-methylphenyl)fluorene thus dissolved show a hue of 1 or less in Gardner. The total amount of toluene used was 4 parts by weight relative to 1 part by weight of the 9,9-bis(4-hydroxy-3-methylphenyl)fluorene.

Example 7

A reaction was carried out by (a) adding 40.0 g of fluorenone, 306.7 g of 2-phenoxyethanol, and 4 g of bentonite clay-K10 (manufactured by ACROS) serving as a catalyst into a 500 ml glass reactor vessel equipped with a stirrer, a condenser and a thermometer and (b) stirring a mixture under a reduced pressure of $4.0 \times 10^3$ Pa at 140° C. for 5 hours while removing generated water out of the system. A reaction liquid was subjected to HPLC, and it was found that the amount of remaining fluorenone was 5.0%. An obtained reaction mixture liquid was filtered, thereby the catalyst was removed. Thereafter, 0.8 g of 29% sodium hydroxide aqueous solution was added, and 240.0 g of 2-phenoxyethanol was distilled away by concentration under reduced pressure. To an obtained concentrated liquid, 280 g of toluene and 60 g of water were added, and the mixture liquid was stirred at 80° C. Thereafter, an aqueous phase was separated and removed, and a target substance partitioned in an organic phase was recovered. Separated waste water was analyzed, and it was found that TOC=790 mg/L, COD=2500 mg/L, BOD=210 mg/L, and phenol content=0.1 mg/L or less.

An obtained organic phase was washed twice with 60 g of water, and thereafter cooled to 20° C. Then, precipitated crystals were subjected to filtration and drying to obtain 68.7 g of 9,9-bis(4-(2-hydroxyethoxy)phenyl)fluorene (yield: 70.6%, LC purity: 98.2%). Obtained 9,9-bis(4-(2-hydroxyethoxy)phenyl)fluorene was dissolved by heat at 230° C. for 2 hours. The 9,9-bis(4-(2-hydroxyethoxy)phenyl)fluorene thus dissolved show a hue of 60 in APHA. The total amount of toluene used in the production was 4.1 parts by weight relative to 1 part by weight of the 9,9-bis[4-(2-hydroxyethoxy)phenyl]fluorene.

Example 8

A reaction was carried out by (a) adding 40.0 g of fluorenone, 306.7 g of 2-phenoxyethanol, and 1.0 g of tungstophosphoric acid to a 500 ml glass reactor vessel equipped with a stirrer, a condenser and a thermometer and (b) stirring a mixture under a reduced pressure of $0.4 \times 10^3$ Pa at 120° C. for 3 hours while removing generated water out of the system. A reaction liquid was subjected to HPLC, and it was found that the amount of remaining fluorenone was 0.3% or less. To an obtained reaction mixture liquid, 0.8 g of 29% sodium hydroxide aqueous solution was added, and thereafter 240.0 g of 2-phenoxyethanol was distilled away by concentration under reduced pressure. To an obtained concentrated liquid, 280 g of toluene and 60 g of water were added, and stirred at 80° C. Thereafter, an aqueous phase was separated and removed, and a target substance partitioned in an organic phase was recovered. Separated waste water was analyzed, and it was found that COD=2100 mg/L, BOD=180 mg/L, and phenol content=0.1 mg/L or less.

The organic phase thus obtained was washed twice with 60 g of water, and thereafter cooled to 20° C. Then, precipitated crystals were subjected to filtration and drying to obtain 78.7 g of 9,9-bis(4-(2-hydroxyethoxy)phenyl)fluorene (yield: 80.8%, LC purity: 99.2%). Obtained 9,9-bis(4-(2-hydroxyethoxy)phenyl)fluorene was dissolved by heat at 230° C. for 2 hour. The 9,9-bis(4-(2-hydroxyethoxy)phenyl)fluorene thus dissolved show a hue of 40 in APHA. The total amount of toluene used in the production was 3.6 parts by weight relative to 1 part by weight of the 9,9-bis(4-(2-hydroxyethoxy)phenyl)fluorene.

Example 9

A reaction was carried out by (a) adding 50 g of fluorenone, 383.4 g of phenoxyethanol, 50 g of toluene, and 1.3 g of tungstophosphoric acid to a glass reactor vessel equipped with a stirrer, a thermometer and a water separator with a condenser and (b) stirring a mixture for 8 hours under a reduced pressure of $13.0 \times 10^3$ Pa at 110° C. under toluene reflux while removing generated water out of the reaction system. A reaction liquid was subjected to HPLC, and it was found that the amount of remaining fluorenone was 0.3% or less. To an obtained reaction mixture liquid, 0.8 g of 29% sodium hydroxide aqueous solution was added, and thereafter toluene and 306.0 g of 2-phenoxyethanol were distilled away by concentration under reduced pressure. To an obtained concentrated liquid, 300 g of toluene and 60 g of water were added, and the mixture liquid was stirred at 80° C. Thereafter, an aqueous phase was separated and removed, and a target substance partitioned in an organic phase was recovered. Separated waste water was analyzed, and it was found that COD=2800 mg/L, BOD=230 mg/L, and phenol content=0.1 mg/L or less.

The organic phase thus obtained was washed twice with 60 g of water, and cooled to 20° C. Then, precipitated crystals were subjected to filtration and drying to obtain 95.1 g of 9,9-bis(4-(2-hydroxyethoxy)phenyl)fluorene (yield: 78.2%, LC purity: 99.0%). Obtained 9,9-bis(4-(2-hydroxyethoxy) phenyl)fluorene was dissolved by heat at 230° C. for 2 hours. The 9,9-bis(4-(2-hydroxyethoxy)phenyl)fluorene thus dissolved show a hue of 40 in APHA. The total amount of toluene used in the production was 3.7 parts by weight relative to 1 part by weight of the 9,9-bis[4-(2-hydroxyethoxy)phenyl]fluorene.

Example 10

A reaction was carried out by (a) adding 23.0 g of fluorenone, 156.4 g of 2,6-dimethylphenol, and 0.6 g of tungstosilicic acid to a 500 ml glass reactor vessel equipped with a stirrer, a condenser and a thermometer and (b) stirring a mixture for 4 hours under a reduced pressure of $1.3 \times 10^3$ Pa at 70° C. while removing generated water out of the reaction system. The amount of remaining fluorenone was determined by HPLC, and found to be 0.1% or less. To an obtained reaction mixture liquid, 0.6 g of 29% sodium hydroxide aqueous solution was added, and 100 g of 2,6-dimethylphenol was recovered from an organic phase by concentration under reduced pressure. To an obtained concentrated liquid, 161 g of toluene and 46 g of water were added, and the mixture liquid was stirred at 80° C. Thereafter, an aqueous phase was separated and removed, and a target substance partitioned in an organic phase was recovered. The organic phase was further washed twice with 46 g of water, and cooled to 10° C. Then, precipitated crystals were subjected to filtration and drying to obtain 45.5 g of 9,9-bis(4-hydroxy-3,5-dimethylphenyl)fluorene (yield: 87.4%, LC purity: 99.6%). Obtained 9,9-bis(4-hydroxy-3,5-dimethylphenyl)fluorene was dissolved by heat at 250° C. for 2 hours. The 9,9-bis(4-hydroxy-3,5-dimethylphenyl)fluorene thus dissolved show a hue of 1 in Gardner. The total amount of toluene used was 3.5 parts by weight relative to 1 part by weight of the 9,9-bis(4-hydroxy-3,5-dimethylphenyl)fluorene.

Example 11

A reaction was carried out by (a) adding 40.0 g (0.222 mol) of fluorenone, 306.7 g (2.22 mol) of 2-phenoxyethanol, and 1.0 g of tungstophosphoric acid [$(H_3PW_{12}O_{40}) \cdot nH_2O$] serving as a catalyst to a glass reactor vessel equipped with a stirrer, a nitrogen-blowing tube, a thermometer and a condenser and (b) allowing a mixture to react for 5 hours under a reduced pressure of $1.3 \times 10^3$ Pa at 120° C. The content of multimers in a reaction mixture obtained after completion of the reaction was 4.5%. To the reaction mixture thus obtained, 400.0 g of toluene was added. The reaction mixture was neutralized with a sodium hydroxide aqueous solution and washed with water. Thereafter an organic phase was separated. Toluene and excess 2-phenoxyethanol were removed from an obtained organic phase by concentration under reduced pressure. To an obtained concentrate, 280.0 g of toluene was added, and the mixture was heated and stirred at 80° C. for 1 hour, and thereafter directly cooled to 65° C. Then, 0.4 g of crystals of 9,9-bis(4-(2-hydroxyethoxy)phenyl)fluorene serving as seed crystals were added, and a mixture was incubated at 65° C. for 2 hours and thereafter directly cooled to 20° C. Then, precipitated crystals were subjected to filtration and drying to obtain 78.3 g of white crystals of 9,9-bis(4-(2-hydroxyethoxy)phenyl)fluorene (yield: 80.4%, purity: 98.3%). The 9,9-bis(4-(2-hydroxyethoxy)phenyl)fluorene thus obtained had a melting point of 163° C.

Example 12

A reaction was carried out by (a) adding 80.0 g (0.444 mol) of fluorenone, 613.5 g (4.44 mol) of 2-phenoxyethanol, and 2.0 g of tungstophosphoric acid [$(H_3PW_{12}O_{40}) \cdot nH_2O$] serving as a catalyst to a glass reactor vessel equipped with a stirrer, a nitrogen-blowing tube, a thermometer and a T-tube and (b) allowing a mixture to react for 4 hours under a reduced pressure of $2.0 \times 10^3$ Pa at 130° C. The content of multimers in a reaction mixture obtained after completion of the reaction was 3.9%. To the reaction mixture thus obtained, 800.0 g of toluene was added. The reaction mixture was neutralized with a sodium hydroxide aqueous solution and washed with water. Thereafter an organic phase was separated. Toluene and excess 2-phenoxyethanol were removed from an obtained organic phase by concentration under reduced pressure. To an obtained concentrate, 560.0 g of toluene was added, and the mixture was heated and stirred at 80° C. for 1 hour and thereafter directly cooled to 70° C. Thereafter, 0.4 g of crystals of 9,9-bis(4-(2-hydroxyethoxy)phenyl)fluorene serving as seed crystals were added, and a mixture was incubated at 70° C. for 2 hours and thereafter directly cooled to 20° C. Then, precipitated crystals were subjected to filtration and drying to obtain 78.0 g of white crystals of 9,9-bis(4-(2-hydroxyethoxy)phenyl)fluorene (yield: 90.2%, purity:

99.2%). The 9,9-bis(4-(2-hydroxyethoxy)phenyl)fluorene thus obtained had a melting point of 163° C.

Example 13

A reaction was carried out by (a) adding 40.0 g (0.222 mol) of fluorenone, 306.7 g (2.22 mol) of 2-phenoxyethanol, and 1.0 g of tungstophosphoric acid [$(H_3PW_{12}O_{40}).nH_2O$] serving as a catalyst to a glass reactor vessel equipped with a stirrer, a nitrogen-blowing tube, a thermometer and a condenser and (b) allowing a mixture to react for 4 hours under a reduced pressure of $2.7 \times 10^3$ Pa at 140° C. The content of multimers in a reaction mixture obtained after completion of the reaction was 5.1%. To the reaction mixture thus obtained, 400.0 g of toluene was added. The reaction mixture was neutralized with a sodium hydroxide aqueous solution and washed with water. Thereafter, an organic phase was separated. Toluene and excess 2-phenoxyethanol were removed from an obtained organic phase by concentration under reduced pressure. To an obtained concentrate, 280.0 g of toluene was added, and the concentrate was heated and stirred at 80° C. for 1 hour and thereafter directly cooled to 65° C. Thereafter, 0.2 g of crystals of 9,9-bis(4-(2-hydroxyethoxy)phenyl)fluorene serving as seed crystals were added, and a mixture was incubated at 65° C. for 2 hours and thereafter directly cooled to 20° C. Then, precipitated crystals were subjected to filtration and drying to obtain 77.3 g of white crystals of 9,9-bis(4-(2-hydroxyethoxy)phenyl)fluorene (yield: 89.9%, purity: 99.0%). The 9,9-bis(4-(2-hydroxyethoxy)phenyl)fluorene thus obtained had a melting point of 163° C.

Example 14

A reaction was carried out by (a) adding 50.0 kg (0.277 kmol) of fluorenone, 384.2 kg (2.78 kmol) of 2-phenoxyethanol, and 1.25 kg of tungstophosphoric acid [$(H_3PW_{12}O_{40}).nH_2O$] serving as a catalyst to a reactor vessel equipped with a stirrer, a nitrogen-blowing tube, a thermometer and a condenser and (b) allowing a mixture to react for 7 hours under a reduced pressure of $2.0 \times 10^3$ Pa at 130° C. The content of multimers in a reaction mixture obtained after completion of the reaction was 5.0%. To the reaction mixture thus obtained, 500.0 kg of toluene was added. The reaction mixture was neutralized with a sodium hydroxide aqueous solution and washed with water. Then, an organic phase was separated. Toluene and excess 2-phenoxyethanol were removed from an obtained organic phase by concentration under reduced pressure. To an obtained concentrated product, 350.0 kg of toluene was added, and the mixture was heated and stirred at 80° C. for 1 hour and thereafter directly cooled to 67° C. Thereafter, 0.3 kg of crystals of 9,9-bis(4-(2-hydroxyethoxy)phenyl)fluorene serving as seed crystals were added, and a mixture was incubated at 67° C. for 2 hours and thereafter directly cooled to 20° C. Then, precipitated crystals were subjected to filtration and drying to obtain 77.5 kg of white crystals of 9,9-bis(4-(2-hydroxyethoxy)phenyl)fluorene (yield: 88.7%, purity: 98.9%). The 9,9-bis(4-(2-hydroxyethoxy)phenyl) fluorene thus obtained had a melting point of 163° C.

Comparative Example 5

A reaction was carried out by (a) adding 86.4 g (0.48 mol) of fluorenone, 397.9 g (2.88 mol) of 2-phenoxyethanol, 350 g of toluene, and 4.3 g of tungstophosphoric acid [$(H_3PW_{12}O_{40})$] serving as a catalyst to a glass reactor vessel equipped with a stirrer, a nitrogen-blowing tube, a thermometer and a water separator with a condenser and (b) allowing a mixture to react for 12 hours at normal pressures under toluene reflux while removing generated water out of the reaction system. The content of multimers in a reaction mixture obtained after completion of the reaction was 9.1%. To a reaction liquid thus obtained, 300 g of toluene was added, and the reaction liquid was washed with 100 g of water at 80° C. An obtained organic phase was gradually cooled to 10° C. Then, precipitated crystals were subjected to filtration and drying to obtain 146.2 g of white crystals of 9,9-bis(4-(2-hydroxyethoxy)phenyl)fluorene (yield: 75.1%, purity: 99.0). The 9,9-bis(4-(2-hydroxyethoxy)phenyl)fluorene thus obtained had a melting point of 109° C. A suspension of 60.0 g of the 9,9-bis(4-(2-hydroxyethoxy) phenyl)fluorene thus obtained and 300.0 g of toluene was heated to 100° C., and stirred for next 1 hour at 100° C. to obtain a uniform solution. The solution was gradually cooled. At 70° C., crystals started to precipitate. The solution was further cooled to 10° C., and stirred for 1 hour while keeping the temperature at 10° C. Then, precipitated crystals were subjected to filtration and drying to obtain 53.9 g of white crystals of 9,9-bis(4-(2-hydroxyethoxy)phenyl)fluorene (yield: 89.9% (total yield 67.5%), purity: 99.5%). The 9,9-bis(4-(2-hydroxyethoxy) phenyl)fluorene thus obtained had a melting point of 163° C.

Comparative Example 6

A reaction was carried out by (a) adding 40.0 kg (0.222 kmol) of fluorenone, 307.0 kg (2.22 kmol) of 2-phenoxyethanol, 160.1 kg of toluene, and 0.92 kg of tungstophosphoric acid [$(H_3PW_{12}O_{40})$] serving as a catalyst to a reactor vessel equipped with a stirrer, a nitrogen-blowing tube, a thermometer and a water separator with a condenser and (b) allowing a mixture to react for 27 hours at normal pressures under toluene reflux while removing generated water out of the reaction system. The content of multimers in a reaction mixture obtained was 12.1%. To the reaction liquid thus obtained, 150.0 kg of toluene was added, and the reaction liquid was washed with 49 kg of water at 80° C. An obtained organic phase was gradually cooled to 10° C. Then, precipitated crystals were subjected to filtration and drying to obtain 71.0 kg of white crystals of 9,9-bis(4-(2-hydroxyethoxy)phenyl)fluorene (yield: 73.0%, LC purity: 97.9%). The 9,9-bis(4-(2-hydroxyethoxy)phenyl)fluorene thus obtained had a melting point of 109° C. A suspension of 59.0 kg of this crude product and 300.0 kg of toluene was heated to 100° C., and stirred for next 1 hour at 100° C. to obtain a uniform solution. The solution was gradually cooled. At 65° C., crystals started to precipitate. The solution was further cooled to 10° C., and stirred for 1 hour while keeping the temperature at 10° C. Then, precipitated crystals were recovered by filtration, and dried under reduced pressure to obtain 51.3 kg of white crystals of 9,9-bis(4-(2-hydroxyethoxy)phenyl)fluorene (yield: 87.0% (total yield 63.5%), purity: 98.7%). The 9,9-bis(4-(2-hydroxyethoxy)phenyl)fluorene thus obtained had a melting point of 163° C.

Comparative Example 7

A reaction was carried out by (a) adding 40.0 g (0.222 mol) of fluorenone, 306.7 g (2.22 mol) of 2-phenoxyethanol, and 1.0 g of tungstophosphoric acid [$(H_3PW_{12}O_{40}).nH_2O$] serving as a catalyst to a glass reactor vessel equipped with a stirrer, a nitrogen-blowing tube, a thermometer and a condenser and (b) allowing a mixture to react for 2 hours at normal pressure at 170° C. The content of multimers in a reaction mixture obtained was 14.0%. To the reaction mixture thus obtained, 400.0 g of toluene was added. The reaction mixture was neutralized with a sodium hydroxide aqueous solution and washed with water. Thereafter, an organic phase was separated. Toluene and excess 2-phenoxyethanol were removed from the organic phase by concentration under reduced pressure. To an obtained concentrate, 280.0 g of toluene was added. The mixture was heated and stirred at 80° C. for 1 hour, and thereafter directly cooled to 0° C. However, the concentrate turned into an oily matter, and no crystals were obtained.

INDUSTRIAL APPLICABILITY

According to a method for producing a fluorene derivative in accordance with the present invention, it is possible to produce a fluorene derivative that reduces the burden on the environment, is suitable for industrial use, and has high purity and good hue.

Therefore, the present invention is not only very useful in chemical industrial fields such as production of fluorene derivatives and production of polymers (e.g., epoxy resin, polyester, polyether, and polycarbonate) using the fluorene derivatives as raw materials, which polymers are excellent in heat resistance and transparency and have a high index of refraction, but also applicable to fields of optical lenses, films, plastic optical fibers, optical disc substrates, heat resistant resin, and engineering plastic etc. which use such polymers.

The invention claimed is:

1. A method for producing a fluorene derivative of formula (II)

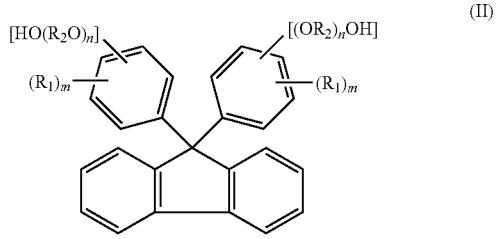

(wherein $R_2$ is an alkylene group; $R_1$ is selected from an alkyl group, a cycloalkyl group, an aryl group, an aralkyl group, an alkoxy group, and a halogen atom; n is 0 or an integer of 1 or greater; and m is 0 or an integer of 1 to 4, with the proviso that when m is 0, n is an integer of 1 or greater)

by reacting fluorenone with a compound of formula (I)

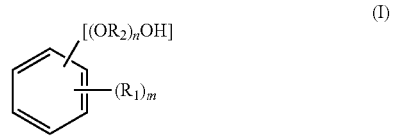

(wherein $R_2$ is an alkylene group; $R_1$ is selected from an alkyl group, a cycloalkyl group, an aryl group, an aralkyl group, an alkoxy group, and a halogen atom; n is 0 or an integer 1 or greater; and m is 0 or an integer of 1 to 4, with the proviso that when m is 0, n is an integer of 1 or greater)

in the presence of an acid catalyst,
said method, comprising the steps of:
reacting the fluorenone with the compound of formula (I) in the presence of the acid catalyst to obtain a reaction mixture liquid that contains the fluorene derivative of formula (II); and
after addition of an alkali to the reaction mixture liquid that contains the fluorene derivative after completion of reaction, concentrating the reaction mixture liquid without removing the alkali thus added and a reaction product of the alkali, thereby separating an unreacted compound of formula (I).

2. The method according to claim 1, wherein, in the step of reacting, the fluorenone and the compound of formula (I) are reacted under reduced pressure.

3. The method according to claim 1, wherein the compound of formula (I) is methyl phenol or phenoxyethanol.

4. The method according to claim 3, wherein:
the compound of formula (I) is phenoxyethanol; and
the fluorenone and the compound of formula (I) are reacted under a reduced pressure of not more than $39 \times 10^3$ Pa at a temperature between 30° C. and 150° C.

5. The method according to claim 3, wherein:
the compound of formula (I) is methyl phenol; and
the fluorenone and the compound of formula (I) are reacted under a reduced pressure of not more than $30 \times 10^3$ Pa at a temperature between 30° C. and 95° C.

6. The method according to claim 1, wherein the unreacted compound of formula (I) separated in the step of concentrating is recycled to the step of reacting so as to be used as a raw material.

7. A method according to claim 1, further comprising the steps of:
extracting the fluorene derivative by adding an extract agent constituted by water and an organic solvent separable from water to a concentrated liquid obtained in the step of concentrating to partition the fluorene derivative into an organic phase, and thereafter separating an aqueous phase; and
precipitating a crystal of the fluorene derivative by cooling the organic phase, and thereafter filtering the organic phase to recover the crystal.

* * * * *